US011775902B2

(12) United States Patent
Baek et al.

(10) Patent No.: US 11,775,902 B2
(45) Date of Patent: *Oct. 3, 2023

(54) SYSTEM AND METHOD TO PREDICT, PREVENT, AND MITIGATE WORKPLACE INJURIES

(71) Applicant: UNIVERSITY OF IOWA RESEARCH FOUNDATION, Iowa City, IA (US)

(72) Inventors: Stephen Baek, Iowa City, IA (US); Nathan B. Fethke, Iowa City, IA (US); Jean Robillard, Iowa City, IA (US); Joseph A. V. Buckwalter, Iowa City, IA (US); Pamela Villacorta, Iowa City, IA (US)

(73) Assignee: UNIVERSITY OF IOWA RESEARCH FOUNDATION, Iowa City, IA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/717,714

(22) Filed: Apr. 11, 2022

(65) Prior Publication Data

US 2022/0237537 A1 Jul. 28, 2022

Related U.S. Application Data

(63) Continuation of application No. 16/825,692, filed on Mar. 20, 2020, now Pat. No. 11,328,239.
(Continued)

(51) Int. Cl.
G06Q 10/0635 (2023.01)
G06Q 10/0631 (2023.01)
(Continued)

(52) U.S. Cl.
CPC ........ *G06Q 10/0635* (2013.01); *G06N 20/00* (2019.01); *G06Q 10/063114* (2013.01); *G06V 40/23* (2022.01)

(58) Field of Classification Search
CPC ...... G06Q 10/0635; G06N 20/00; G06N 3/00; G06N 3/08; G06K 9/00342; G06K 9/00;
(Continued)

(56) References Cited

U.S. PATENT DOCUMENTS 9,566,004 B1    2/2017  Radwin
2009/0030767 A1 1/2009  Morris
(Continued)

OTHER PUBLICATIONS

Herrington et al. "The effect of patella taping on vastus medialis oblique and vastus laterialis EMG activity and knee kinematic variables during stair descent." In: Journal of Electromyography and Kinesiology. May 27, 2005 (May 27, 2005) Retrieved on Jun. 29, 2020 (Sep. 29, 2020) from <URL: https://pubmed.ncbi.nlm.nih.gov/16061396/>.
(Continued)

*Primary Examiner* — Mehmet Yesildag
*Assistant Examiner* — Ayanna Minor
(74) *Attorney, Agent, or Firm* — Ballard Spahr LLP

(57) ABSTRACT

A prevention and safety management system utilizes a non-intrusive imaging sensor (e.g. surveillance cameras, smartphone cameras) and a computer vision system to record videos of workers not wearing sensors. The videos are analyzed using a deep machine learning algorithm to detect kinematic activities (set of predetermined body joint positions and angles) of the workers and recognizing various physical activities (walk/posture, lift, push, pull, reach, force, repetition, duration etc.). The measured kinematic variables are then parsed into metrics relevant to workplace ergonomics, such as number of repetitions, total distance travelled, range of motion, and the proportion of time in
(Continued)

different posture categories. The information gathered by this system is fed into an ergonomic assessment system and is used to automatically populate exposure assessment tools and create risk assessments.

20 Claims, 10 Drawing Sheets

Related U.S. Application Data

(60) Provisional application No. 62/912,895, filed on Oct. 9, 2019, provisional application No. 62/833,438, filed on Apr. 12, 2019.

(51) Int. Cl.
*G06N 20/00* (2019.01)
*G06V 40/20* (2022.01)

(58) Field of Classification Search
CPC .. G06K 9/6201; G06K 9/6285; G06K 9/6289; G06T 7/00; G06T 1/60; G06T 7/20; G16H 50/30; G06V 40/23
See application file for complete search history.

(56) References Cited

U.S. PATENT DOCUMENTS

| | | |
|---|---|---|
| 2011/0199291 A1 | 8/2011 | Tossell |
| 2016/0070958 A1 | 3/2016 | Whelan |
| 2017/0169687 A1 | 6/2017 | Kozloski et al. |
| 2017/0206431 A1* | 7/2017 | Sun .................. G06F 18/24 |
| 2017/0296129 A1* | 10/2017 | Petterson ............ A61B 5/7278 |
| 2018/0014771 A1 | 1/2018 | Merchant-Borna |
| 2018/0024641 A1* | 1/2018 | Mao ................. A63F 13/428 382/103 |
| 2018/0039745 A1* | 2/2018 | Chevalier ............ G16H 30/20 |
| 2018/0255290 A1* | 9/2018 | Holzer ............... H04N 13/221 |
| 2019/0012531 A1 | 1/2019 | Radwin et al. |
| 2019/0012794 A1 | 1/2019 | Radwin et al. |
| 2019/0138967 A1* | 5/2019 | Akella ........... G06Q 10/063112 |
| 2020/0178851 A1* | 6/2020 | Singhose ............ A61B 5/1121 |
| 2020/0273580 A1 | 8/2020 | Kaszuba |

OTHER PUBLICATIONS

Dwivedi. "People Tracking using Deep Learning." In: Medium. Feb. 7, 2019 (Feb. 7, 2019) Retrieved on Jun. 29, 2020 (Sep. 29, 2020) from <https://towardsdatascience.com/people-tracking-using-deep-learning-5c90d43774be>.

International Search Report and Written Opinion issued by the International Searching Authority dated Aug. 20, 2020, for PCT/US2020/023933, filed on Mar. 20, 2020 (14 pages).

European Search Report and Written Opinion dated Nov. 24, 2022, issued by the EPO for EP 20788045.1 (7 pages).

* cited by examiner

SYSTEM AND METHOD TO PREDICT, PREVENT, AND MITIGATE WORKPLACE INJURIES

CROSS REFERENCE TO RELATED APPLICATIONS

This application is a continuation of U.S. Non-Provisional application Ser. No. 16/825,692, filed on Mar. 20, 2020, which claims priority under 35 U.S.C. § 119(e) as a non-provisional of U.S. Provisional Application Ser. No. 62/833,438, filed on Apr. 12, 2019, and as a nonprovisional of U.S. Provisional Application Ser. No. 62/912,895, filed on Oct. 9, 2019, the entireties of which are hereby incorporated by reference herein.

FIELD OF THE INVENTION

The present disclosure and invention pertain to a non-intrusive data gathering system of worker's data of multiple joints, and simultaneously assessing risks associated with the measured movements and exertions to make safety assessments and recommendations.

BACKGROUND

According to the 2018 Liberty Mutual Workplace Safety Index, US businesses spend more than a billion dollars a week on serious non-fatal injuries of employees or over $60 billion per year in direct costs, or about $37,000 per incident. In the state of Iowa alone, the total amount paid for worker's compensation was over $617 million dollars in 2015. Multiple studies have also demonstrated that upper extremities musculoskeletal disorders associated with repetitive motion, forceful tasks, and the combination of repetition and force are the nation's most common and costly occupational health problem. They cost an average of $20 billion annually in workers compensation, and another $100 billion in lost productivity, employee turnover, and other indirect expenses.

As an example, the meat packing industry is ranked number one among the top ten industries with musculoskeletal injury due to repetitive and forceful tasks with an incidence of 9.2 incidents per 100 workers. However, the meat packing industry is only one of many industries where workers engage in multiple repetitive tasks associated with manufacturing systems that need careful risk assessments.

Data from workplace assessment is useful in providing proper safety equipment for interaction with machines and is useful in the insurance industry, particularly workers compensation insurance and rate determination.

There have been many approaches to assessing worker risk and many of the assessment analysis systems involve workers wearing sensors for data collection. The systems that rely on workers wearing sensors are of limited value for many reasons. In the first place, the sensor may alter the worker-measured motions and postures to provide false data. Secondly, many workers do not like the sensation of wearing the sensors which some note to be uncomfortable. Third, the sensors are of course expensive. There is therefore a need for risk assessment systems that do not involve workers wearing sensors.

Other limitations common to available systems include the inability to monitor and provide meaningful assessments from multiple joints simultaneously. If one can measure multiple joints simultaneously it is more cost effective and provides additional data for a more accurate safety management system.

In summary, there is a continuing need for assessment systems which not only do not involve workers wearing sensors, but also which have the advantage of measuring with accuracy multiple joints at one time, and which allow the insured businesses to identify risk for unsafe situations to provide accurate feedback reports. The present invention has as its primary objective fulfilling of these unfilled needs.

Examples of state-of-the-art systems which have these mentioned deficiencies in one method or another include, but are not limited to, Radwin, et al., U.S. 2019/0012794A1 and U.S. 2019/0012531A1. This system does not involve wearer sensors and is a video system limited to data collection focusing on a single body part of the worker, for example hands. Specifically, such systems rely on using changes in the aspect ratio of a bounding box as an indicator of activity level. They lack the ability to monitor joint angles or to recognize specific worker postures. They are also incapable of multiple joint or worker assessments simultaneously. Other examples of the state of art include systems with wearable sensors such as IBM U.S. Pat. No. 10,032,352 and MakuSafe Corporation's U.S. Pat. No. 10,096,230.

Musculoskeletal disorders (MSDs) are a persistent and burdensome occupational health problem among workers in virtually all industry sectors. Occupational, or 'work-related,' MSDs are those that occur as a consequence of exposure to conditions of work (i.e., biomechanical risk factors) that increase mechanical loads on internal musculoskeletal structures, such as working with extremes of posture, high movement speeds, repetitive activities, forceful manual exertions, and combinations of these. In 2017, data compiled by the Bureau of Labor Statistics indicated that work-related MSDs accounted for more than 30% of all nonfatal occupational injuries and illnesses involving lost workdays, with an incidence rate of 30.5 cases per 10,000 full-time equivalent workers. Examples of common work-related MSDs include carpal tunnel syndrome, lateral epicondylitis, medical epicondylitis, rotator cuff tendonitis, De Quervain's tenosynovitis, and non-specific low back pain. Work-related MSDs are generally classified as illnesses rather than injuries, in that their development is typically not the result of an acute trauma but instead the result of prolonged exposure to biomechanical risk factors.

In occupational safety and health practice, 'exposure assessment' refers to the process of quantifying worker exposure to biomechanical risk factors. Information about exposure can be collected directly from workers using interviews, questionnaires, or other forms of self-report. Information about exposure can also be obtained through the use of one or more structured observation-based exposure assessment tools, such as the Strain Index, the Rapid Upper Limb Assessment, the Rapid Entire Body Assessment, the American Conference of Governmental Industrial Hygienists (ACGIH) Threshold Limit Value® (TLV) for Hand Activity, the Occupational Repetitive Actions Index, and, when workers are performing manual materials handling tasks, the ACGIH TLV for Lifting and the National Institute for Occupational Safety and Health (NIOSH) Lifting Equation. Information about exposure can also be obtained by attaching sensors to workers. A benefit of direct measurement is that time series posture and movement information can be summarized by any number of metrics describing exposure magnitude, frequency, and/or variation. C examples include use of the Lumbar Motion Monitor to measure kinematics of the lumbar spine, electrogoniometers to measure angular displacement of certain joints (e.g., most commonly the wrist, but also the knee, shoulder, and elbow), accelerometers to measure the inclination of the trunk or elevation of the upper arm with respect to gravity, inertial measurement units to measure orientation of body segments in three-dimensional space, and surface electromyography to measure muscle activity. Obtaining information about exposure using sensors is referred to as 'direct measurement.'

Measurement of worker postures and movements is a fundamental aspect of virtually all biomechanical exposure assessment methods used in contemporary occupational safety and health practice. Direct measurement is generally accepted as more accurate and precise, and thus more desirable, than self-report or observation-based approaches. However, attaching sensors to workers may alter natural patterns of movement, introducing errors into the resulting measurement data. Furthermore, direct measurements provide data streams limited to a narrow measurement objective and do not capture the overall context of the work activity that observation provides. For this reason, video data collection is a component of many observation-based exposure assessment tools designed for practitioners.

The method described herein represents a substantial improvement to current biomechanical exposure assessment methods. Specifically, the method offers the same benefits of measurement (i.e., accurate and precise time series posture data) without the need to attach sensors to workers and while retaining visual information about the context of the work being assessed that is valued by practitioners for interpretation. For example, the moment of the most extreme postures, which may be associated with peak biomechanical loads, can be easily documented for future work modification interventions. Consequently, the method offers the advantages of both direct measurement and observation-based methods while mitigating the most important limitations of both approaches.

Another key advantage of the method is its ability to produce time series data simultaneously from all body joints within the camera field of view. This capability drastically reduces the human resources burden associated with observation-based exposure assessment. The person-time required to perform observation-based exposure assessment of a single work task has been reported to range from 30 to 170 minutes. Consequently, the overall costs of observation-based exposure assessment are usually greater than the costs of self-report or direct measurement methods. The method performs analyses in near real-time, reducing the overall cost and increasing the practicality of exposure assessment.

SUMMARY

It is to be understood that both the following general description and the following detailed description are exemplary and explanatory only and are not restrictive. A system and method are provided for a Prevention and Safety Management (PSM) system and method for automated analysis of ergonomics for workers in the manufacturing industry using computer vision and deep machine learning. Using this system which does not rely upon wearable sensors (including passive sensors such as visual markers or reflectors), occupational safety engineers in manufacturing plants are able to assess in real time the kinematic aspects of the workers (joint positions and angles for multiple joints simultaneously), and the impact of various physical activities (posture, repetition, force, pull, reach . . . ), to determine the risks of injuries from repetitive motion to shoulder, elbow, wrist, and hand, and to reduce and possibly prevent work-related injuries from happening. Furthermore, by integrating the data generated by the system with plant environmental information and selective workers demographic and health data (precursor conditions), occupational safety engineers are able to act proactively to prevent and mitigate work-related injuries and increase workers' safety.

The invention in some embodiments is a computer vision system that is non-invasive and highly adaptable to many environments for capturing and analyzing ergonomic data without the need for sensors. It permits sensing and evaluating the risk exposure of individual workers as well as capturing and creating a set of data related to a population of workers.

According to one embodiment, a method of evaluating workplace worker injury risks includes videotaping a worker who is not wearing any motion sensors, and who is engaged in routine repetitive movements, to provide recorded videos as input data. The recorded videos are analyzed to resolve multiple joints of the worker. The recorded videos are analyzed for measurable kinematic variables related to each joint. The measurable kinematic variables are analyzed to provide job risk assessment reports as output. The kinematic variables may include at least some of joint positions, angles, range of motion, walking, posture, push, pull, reach, force, repetition, duration, musculoskeletal health, movement velocity, rest/recovery time and variations in movement patterns. Additional workers may be monitored simultaneously but reported on separately. The method may include an ergonomic assessment as well as an assessment of kinematic variables. The method may output data assessment reports with health and risk recommendations.

According to another embodiment, a system for assessing worker injury risks includes an image capturing device that captures image data of a first worker performing repetitive tasks and a computing device in communication with the image capturing device to receive image data from the image capturing device. The computing device is adapted to use a deep machine learning algorithm applied to the image data, without using data from wearable sensors on the worker, to determine a set of joint positions and body angles of the worker. The computing device is further adapted to parse the set of joint positions and body angles into metrics relevant to workplace ergonomics. The computing device is also further adapted to automatically populate a worker risk assessment tool with the metrics relevant to workplace ergonomics in order to make a worker risk assessment. The computing device may be a computing cloud. The image capturing device may be adapted to simultaneously capture images of the first worker and a second worker performing repetitive tasks and to detect the predetermined set of joint positions and body angles of the second worker using a deep machine learning algorithm applied to the image data without using data from wearable sensors on the second worker. The computing device may be further adapted to parse the joint positions and body angles of the second worker into metrics relevant to workplace ergonomics and to automatically populate the worker risk assessment tool with the metrics related to the second worker in order to make a second worker risk assessment. The metrics relevant to workplace ergonomics may comprise posture categories, movement velocities, rest times, and/or variations in movement patterns. The computing device may be further adapted to recommend a course of action to address risks identified in the worker risk assessment. The computing device may be further adapted to use the deep machine learning algorithm applied to the image data, without using data from wearable sensors, to determine ergonomic data related to posture, lift, pull, reach, force, repetition, and duration. The worker risk assessment may include information about the grade and risk of injuries to the worker.

While the present manufacturing revolution has centered mainly around manufacturing processes, effectiveness and operations; for many technical and operational reasons, has not yet focused on improving worker safety and decreasing work-related injuries. This invention using the power of data analytics and cognitive technologies combined with computer vision and deep learning, resets benchmarks for worker safety and is an inflection point about how manufacturer will prevent work-related injuries in the future. Moreover, it is a pragmatic solution which has a very high impact on worker safety and does not require large investments. It can be seen the invention accomplishes its intended objectives.

BRIEF DESCRIPTION OF THE DRAWINGS

The accompanying drawings, which are incorporated in and constitute a part of this specification, show examples and together with the description, serve to explain the principles of the methods, apparatuses, and systems.

DETAILED DESCRIPTION

Figure 1:
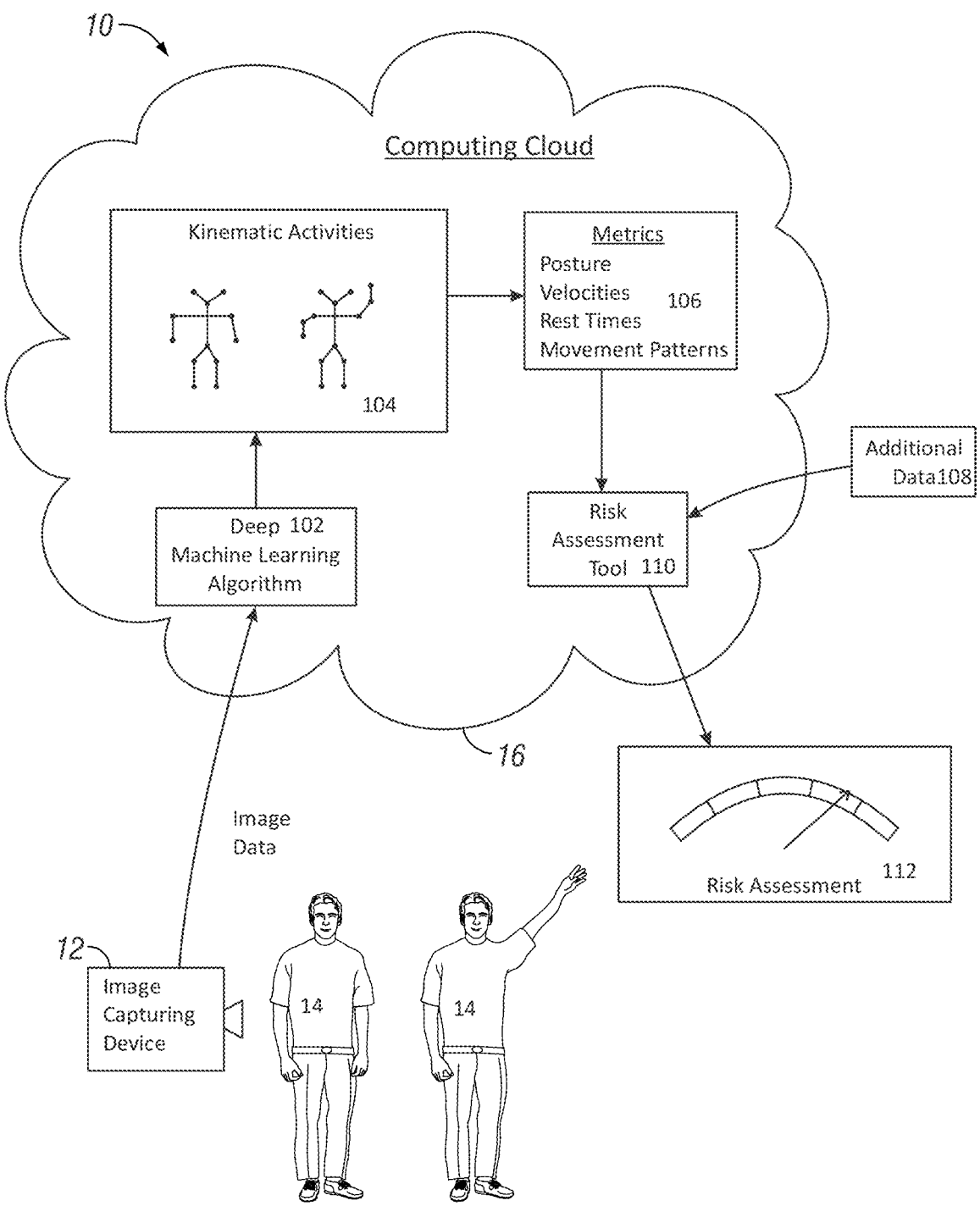
FIG. 1 is a graphic illustration of a system for assessing worker injury risks.

As used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another configuration includes from the one particular value and/or to the other particular value. Similarly, when values are expressed as approximations, by use of the antecedent "about," it will be understood that the particular value forms another configuration. It will be further understood that the endpoints of each of the ranges are significant both in relation to the other endpoint, and independently of the other endpoint.

"Optional" or "optionally" means that the subsequently described event or circumstance may or may not occur, and that the description includes cases where said event or circumstance occurs and cases where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal configuration. "Such as" is not used in a restrictive sense, but for explanatory purposes.

It is understood that when combinations, subsets, interactions, groups, etc. of components are described that, while specific reference of each various individual and collective combinations and permutations of these may not be explicitly described, each is specifically contemplated and described herein. This applies to all parts of this application including, but not limited to, steps in described methods. Thus, if there are a variety of additional steps that may be performed it is understood that each of these additional steps may be performed with any specific configuration or combination of configurations of the described methods.

As will be appreciated by one skilled in the art, hardware, software, or a combination of software and hardware may be implemented. Furthermore, a computer program product on a computer-readable storage medium (e.g., non-transitory) having processor-executable instructions (e.g., computer software) embodied in the storage medium. Any suitable computer-readable storage medium may be utilized including hard disks, CD-ROMs, optical storage devices, magnetic storage devices, memresistors, Non-Volatile Random Access Memory (NVRAM), flash memory, or a combination thereof.

Throughout this application reference is made block diagrams and flowcharts. It will be understood that each block of the block diagrams and flowcharts, and combinations of blocks in the block diagrams and flowcharts, respectively, may be implemented by processor-executable instructions. These processor-executable instructions may be loaded onto a general purpose computer, special purpose computer, or other programmable data processing apparatus to produce a machine, such that the processor-executable instructions which execute on the computer or other programmable data processing apparatus create a device for implementing the functions specified in the flowchart block or blocks.

These processor-executable instructions may also be stored in a computer-readable memory that may direct a computer or other programmable data processing apparatus to function in a particular manner, such that the processor-executable instructions stored in the computer-readable memory produce an article of manufacture including processor-executable instructions for implementing the function specified in the flowchart block or blocks. The processor-executable instructions may also be loaded onto a computer or other programmable data processing apparatus to cause a series of operational steps to be performed on the computer or other programmable apparatus to produce a computer-implemented process such that the processor-executable instructions that execute on the computer or other programmable apparatus provide steps for implementing the functions specified in the flowchart block or blocks.

Accordingly, blocks of the block diagrams and flowcharts support combinations of devices for performing the specified functions, combinations of steps for performing the specified functions, and program instruction means for performing the specified functions. It will also be understood that each block of the block diagrams and flowcharts, and combinations of blocks in the block diagrams and flowcharts, may be implemented by special purpose hardware-based computer systems that perform the specified functions or steps, or combinations of special purpose hardware and computer instructions. This detailed description may refer to a given entity performing some action. It should be understood that this language may in some cases mean that a system (e.g., a computer) owned and/or controlled by the given entity is actually performing the action.

Described herein is a prevention and safety management (PSM) system 10 that utilizes a non-intrusive imaging sensor 12 (e.g. surveillance cameras, smartphone cameras) and a computer vision system to record videos of manufacturing workers performing tasks during their shifts (see FIG. 1). The videos are then analyzed using a deep machine learning algorithm for detecting the kinematic activities (set of predetermined body joint positions and angles) of the workers and recognizing various physical activities (walk/posture, lift, push, pull, reach, force, repetition, duration etc.). The measured kinematic variables are then parsed into metrics relevant to workplace ergonomics, such as number of repetitions, total distance travelled, range of motion, and the proportion of time in different posture categories. The information gathered by this system feed into an ergonomic assessment system and is used to automatically populate current exposure assessment tools to create a risk assessment.

FIG. 1 is a graphical representation of a prevention and safety management system 10. An imaging capturing device 12 is positioned to capture video of workers 14 performing work-related tasks. For example, the workers 14 could be workers in a meat processing facility or other manufacturing process. The image capturing device 12 may be any device that captures video, such as a surveillance camera, a smart phone camera, or any digital video recorder. The system 10 does not require any exact positioning of the image capturing device 12, but direct overhead views may not work. Most oblique views of the workers 14 are useful as long as a clear unobstructed line of sight exists between the camera and the body parts that are desired to be monitored. The system 10 may be able to resolve partially impaired views. As will be explained in greater detail, it is not necessary for the workers 14 to have any sort of markers, reflectors, or sensors attached to their body. Instead, the workers 14 can perform their tasks normally without interference or hinderance from the system.

With further reference to FIG. 1, the image capturing device 12 transmits image data (e.g., AVI, Flash Video, MPEG, WebM, WMV, GIF, and other known video data formats) to a computing device, such as a computing cloud 16. The computing device 16 uses deep machine learning algorithms to resolve the image data into kinematic activities. The computing device 16 is adapted to perform unique analyses of the resolved kinematic activities of multiple body joints simultaneously and make assessments of ergonomic metrics including joint positions and angles, walk/posture, lift, push, pull, reach, force, repetition, duration, and to distinguish and report on each one separately. These ergonomic metrics are analyzed by a computing device 16 adapted to act as a risk assessment tool by applying existing ergonomic models to the ergonomic metrics to create a risk assessment of the workers. The risk assessment may be a score, a risk level, or similar report.

Multiple workers 14 can also be monitored simultaneously if needed. Aspects of the invention in some embodiments include identification of specific individuals, such as workers, tracking of each individual worker, reidentification of persons already in the database, tracking of joints and other landmarks of each person to create wave forms for such joints and landmarks, and assessing and evaluating risks or other parameters of the workers. These aspects are accomplished through an analysis of video images of the workers in a nonlaboratory setting without the need for the workers to wear special markers.

With further reference to FIG. 1, the computing cloud 16 may include a machine learning module 102 and a risk assessment tool 110. The machine learning module 102 may be configured to utilize various machine learning techniques to analyze video and motion data captured using the image capturing device 12. The machine learning module 102 may indicate to the risk assessment tool 110 a level of risk associated with ergonomic movement captured in the video and motion data. The risk assessment tool 110 may receive additional data 108. The risk assessment tool 110 may indicate a risk assessment 112 based on the level of risk.

The videos and other data captured by the PSM system may then be analyzed by the machine learning module 102 using a convolutional neural network algorithm, or a similar algorithm. The machine learning module 102 may take empirical data as an input and recognize patterns within the data. As an example, the empirical data may be the captured video and motion data, and the machine learning module 102 may recognize patterns of kinematic movements of the workers. The captured video and motion data may include a plurality of performance metrics/features 106 determined by an activities module 104. Each of the plurality of performance metrics/features 106 may include a name for each metric/feature and a corresponding coefficient for each metric/feature. The coefficient for a metric/feature may indicate a relative weight of importance of the metric/feature with respect to its impact on ergonomic movement of a worker. The machine learning module 102 may determine a subset of the plurality of performance metrics/features 106 that have the most impact on the ergonomic movement of a worker.

The machine learning model 102 may include parameters, such as the plurality of performance metrics/features 106 that are optimized by the machine learning module 102 for minimizing a cost function associated with the machine learning model given the video and motion data. For instance, in the context of classification, the machine learning model may be visualized as a straight line that separates the video and motion data into two classes (e.g., labels). The cost function may consider a number of misclassified points of the video and motion data. The misclassified points may be a plurality of data points (e.g., one or more performance metrics) that the machine learning model incorrectly classifies as not meeting or exceeding a threshold. A learning process of the machine learning model may be employed by the machine learning module 102 to adjust coefficient values for the parameters/metrics such that the number of misclassified points is minimal. After this optimization phase (e.g., learning phase), the machine learning model may be used to classify new data points 508 for a test of video and motion data.

The machine learning module 102 may employ one or more supervised, unsupervised, or semi-supervised machine learning models. Generally, supervised learning entails the use of a training set of data that may be used to train the machine learning model to apply labels to the input data. For example, the training data may include performance data containing a plurality of data points (e.g., performance metrics) that may, or may not, meet the performance threshold and may be labeled as such. Unsupervised techniques, on the other hand, do not require a training set of labels. While a supervised machine learning model may determine whether previously seen patterns in a training dataset have been correctly labeled in a testing dataset, an unsupervised model may instead determine whether there are sudden changes in values of the plurality of data points. Semi-supervised machine learning models take a middle ground approach that uses a greatly reduced set of labeled training data as known in the art.

The machine learning module 102 may employ one or more machine learning algorithms such as, but not limited to, a nearest neighbor (NN) algorithm (e.g., k-NN models, replicator NN models, etc.); statistical algorithm (e.g., Bayesian networks, etc.); clustering algorithm (e.g., k-means, mean-shift, etc.); neural networks (e.g., reservoir networks, artificial neural networks, etc.); support vector machines (SVMs); logistic or other regression algorithms; Markov models or chains; principal component analysis (PCA) (e.g., for linear models); multi-layer perceptron (MLP) ANNs (e.g., for non-linear models); replicating reservoir networks (e.g., for non-linear models, typically for time series); random forest classification; a combination thereof and/or the like. The machine learning module 102 may include any number of machine learning models to perform the techniques herein, such as for cognitive analytics, predictive analysis, and/or trending analytics as known in the art.

Figure 2:
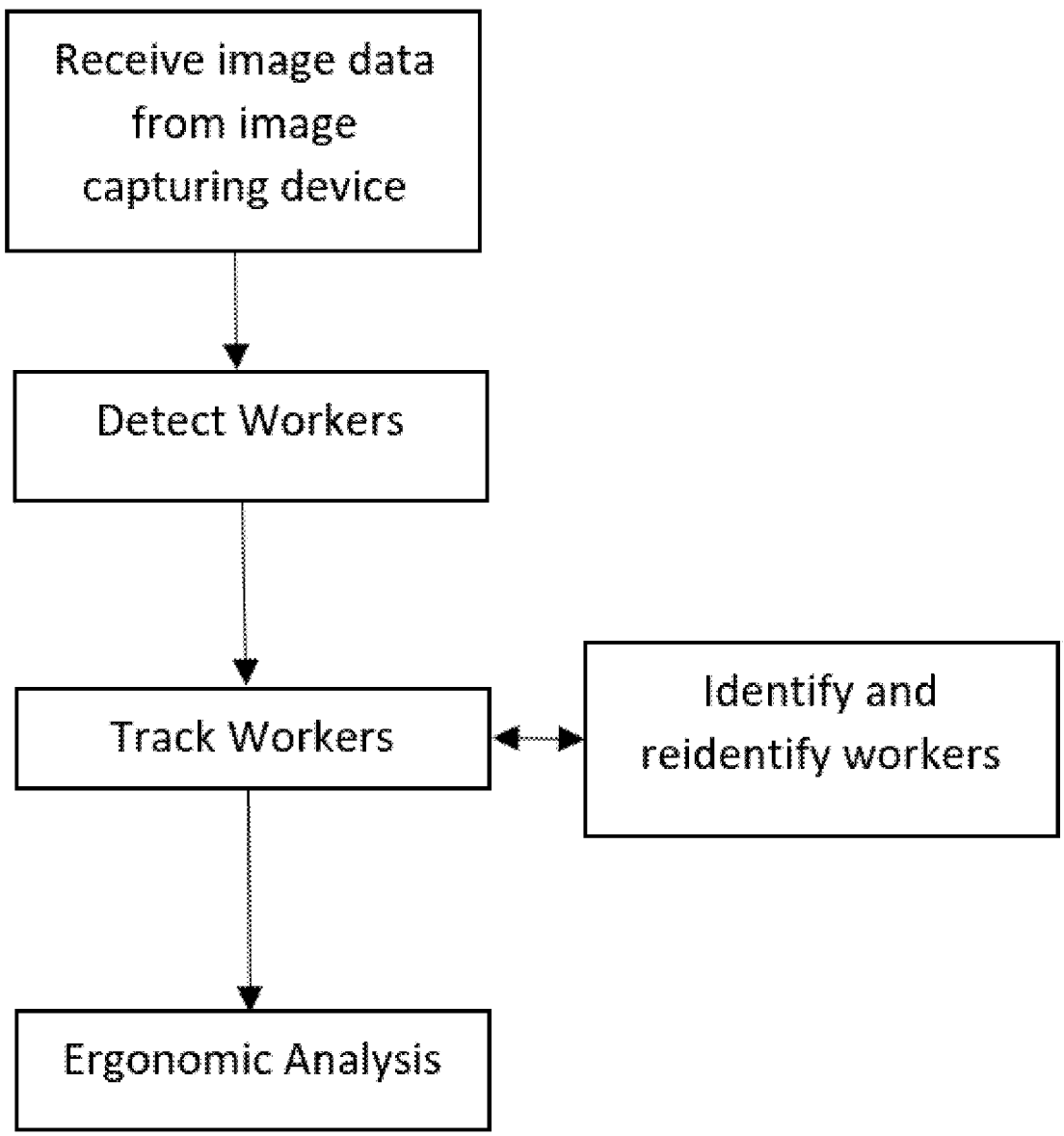
FIG. 2 is a flow chart showing an algorithm used to perform an assessment of worker injury risks.

FIG. 2 illustrates an algorithm used to perform worker risk assessments according to one embodiment of the invention. As illustrated, a computing device such as a computer or computing cloud receives image data from an image capturing device. The computing device is adapted to detect workers within the image data. The detected workers movements are tracked within the image data. Workers are identified and assigned a file identity within a database such that all tracked movements made by a single worker are saved in a record within the database associated with that worker. The tracked movements are analyzed using ergonomic analysis tools to generate worker risk assessments.

Detection of Workers

Figure 3:
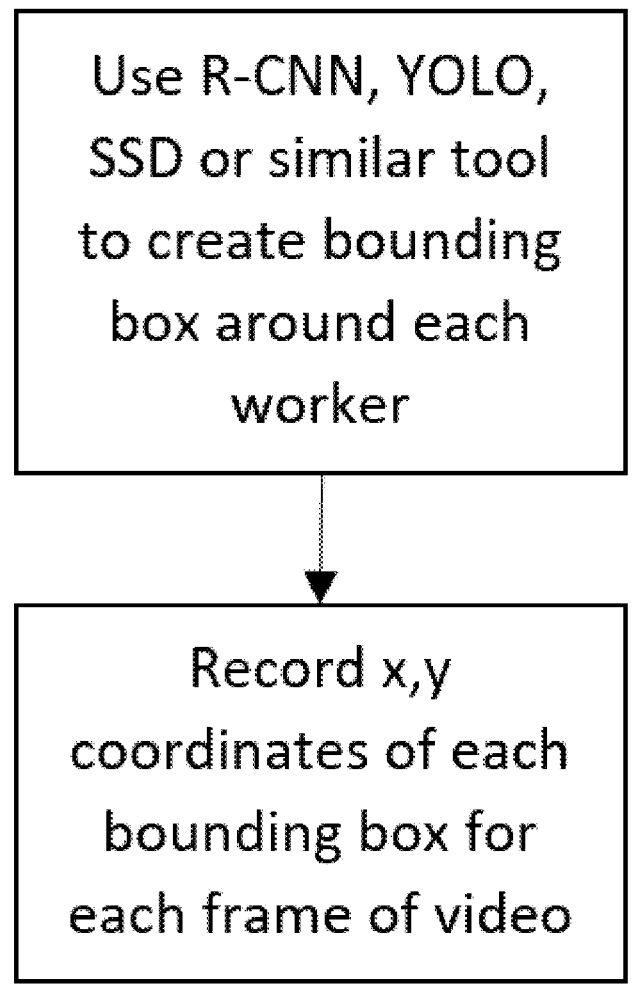
FIG. 3 is a flow chart showing an algorithm performed on a computing device to detect workers.
Figure 4:
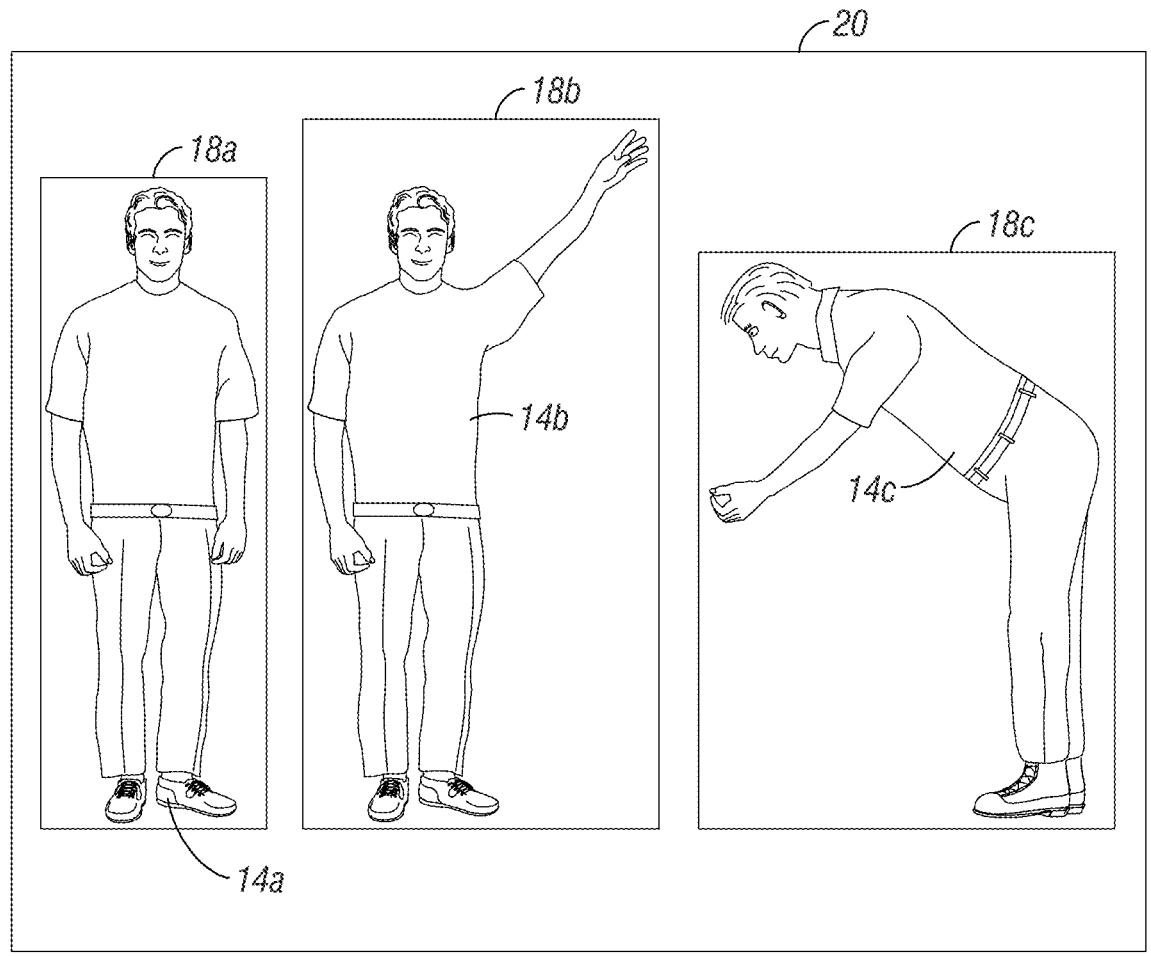
FIG. 4 shows a video frame created from image data showing three workers surrounded by bounding boxes.

FIG. 3 shows an algorithm performed on the computing device 16 to detect workers. Individual workers 14 are detected by using a region-based frame-by-frame analysis of the video stream. In particular, bounding boxes are generated around each person detected in the image data. FIG. 4 shows a video frame 20 created from the image data wherein three workers 14a, 14b, and 14c are surrounded by bounding boxes 18a, 18b, and 18c. A preferred method for generating the bounding boxes uses a region-based convolutional neural network (R-CNN) and its variants (Faster R-CNN, Mask R-CNN, etc.) to detect workers and create the bounding boxes 18a, 18b, and 18c. Alternatively, YOLO (you only look once) or SSD (single shot detection) mechanisms may be used to detect individual workers 14 and generate bounding boxes 18. Those of skill in the art will be aware of numerous acceptable alternatives for generating a bounding box 18 around each worker 14. The bounding boxes are identified by x-y coordinates, (i.e., width, and height) within each frame of the video. The coordinates of each bounding box are recorded in a computer database on a frame-by-frame basis.

A neural network is a computational model that comprises artificial neurons that produces a numerical value, called activation, for given input stimuli. There can be layers of artificial neurons in an artificial neural network model. Each layer produces output activations, which are then fed into the next layer as input stimuli. The earliest layer in the stack of artificial neurons receives pixel values of an image as input, whereas the latest layer produces a processed output. The neurons are connected to each other across layers, whose strength of connection is determined by tunable coefficients that are trained from data. CNNs are a species of artificial neural networks that can be characterized as local connection of neurons. That is, unlike other artificial neural networks, where neurons are connected to all the other neurons in their previous layer, neurons in CNNs are connected to a small, localized window. In addition, neurons in a CNN layer are aligned in a grid layout, as opposed to a one-dimensional layout as in other neural networks, presenting the advantage of preserving spatial structure of activations.

As such, CNNs produce a spatial map of activations per each corresponding receptive field window. The weighting of connections within a receptive field window determines what type of visual patterns that an activation map responds to. A convolution layer typically produces multiple such activation map, each of which specializes in certain visual patterns. In a stack of convolution layers, earlier layers tend to pick up geometric primitives such as edges, ridges, and blobs, while deeper layers combine those primitive responses and construct more abstract, high-level semantic features. Hence, with the activation maps at different depths of a CNN, one can create a multi-level visual summary of the image being analyzed.

Depending on the way of stacking convolution layers, there can be different architectures of CNNs. Some of the popular architectures in generic computer vision tasks include AlexNet, VGG networks, Residual Networks (ResNet), and Densely-connected Networks (DenseNet). These architectures have deep stack of layers with a large number of tunable parameters. Hence, training of these architectures requires a massive number of data. To this end, large image data bases such as ImageNet and MS-COCO are often used to train those architectures.

A CNN backbone produces a set of activation maps that summarizes visual features and patterns at different levels. An individual activation map may be denoted with a matrix $F\_(i=1, \ldots, m)$ of size $H\_i \times W\_i$. The set of activation maps $F=\{F\_i\}$ produced by a CNN backbone serves as a preprocessed input to the other building blocks discussed below.

Tracking

Figure 5:
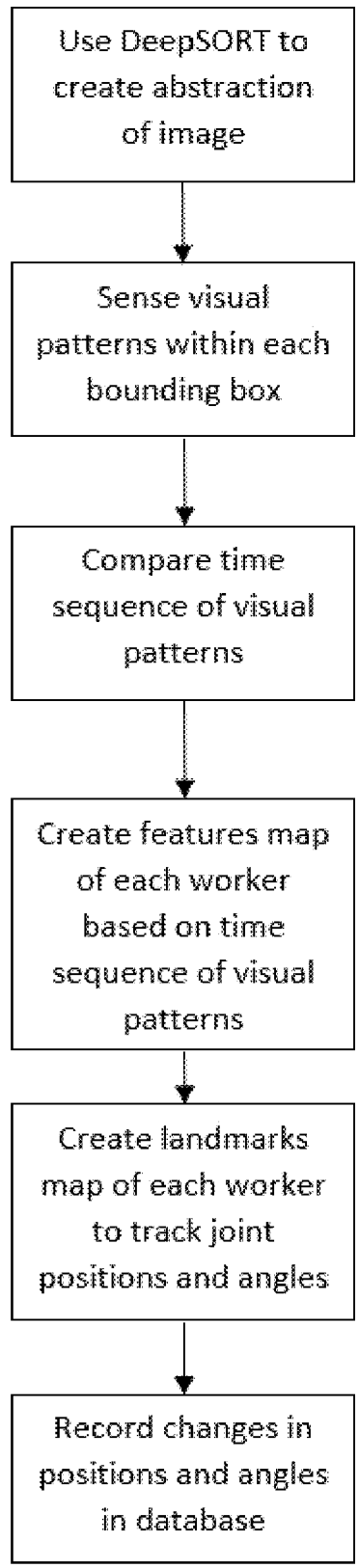
FIG. 5 is a flow chart showing an algorithm performed on a computing device to track workers in a video.

Each of the identified workers 14 within a bounding box 18 is then tracked by the computing device 16 using the algorithm shown illustrated in FIG. 5. The preferred framework for tracking the workers is DeepSORT (a type of Simple Realtime Tracker that relies on deep machine learning). DeepSORT uses convolutional neural networks to create an abstraction of the image within each bounding box. In essence, the DeepSORT framework senses visual patterns within the bounding boxes and compares the visual patterns within a time sequence of consecutive images. The DeepSORT framework extracts a feature map within each bounding box. As a result, each worker has a unique feature map that can be used to identify and track the worker and his or her features within the video stream. This feature map may be saved in a database and assigned as a unique employee profile.

Figure 6:
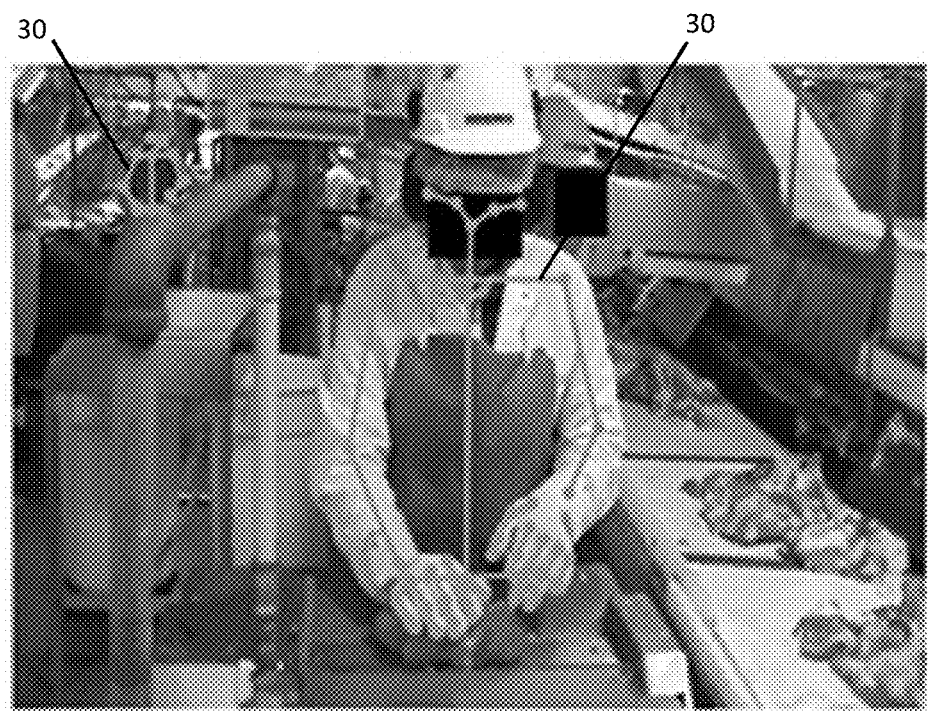
FIG. 6 illustrates a feature map of a worker generated on an image of a video feed of a worker that has been detected and tracked based on image data sent to the computing device.
Figure 7:
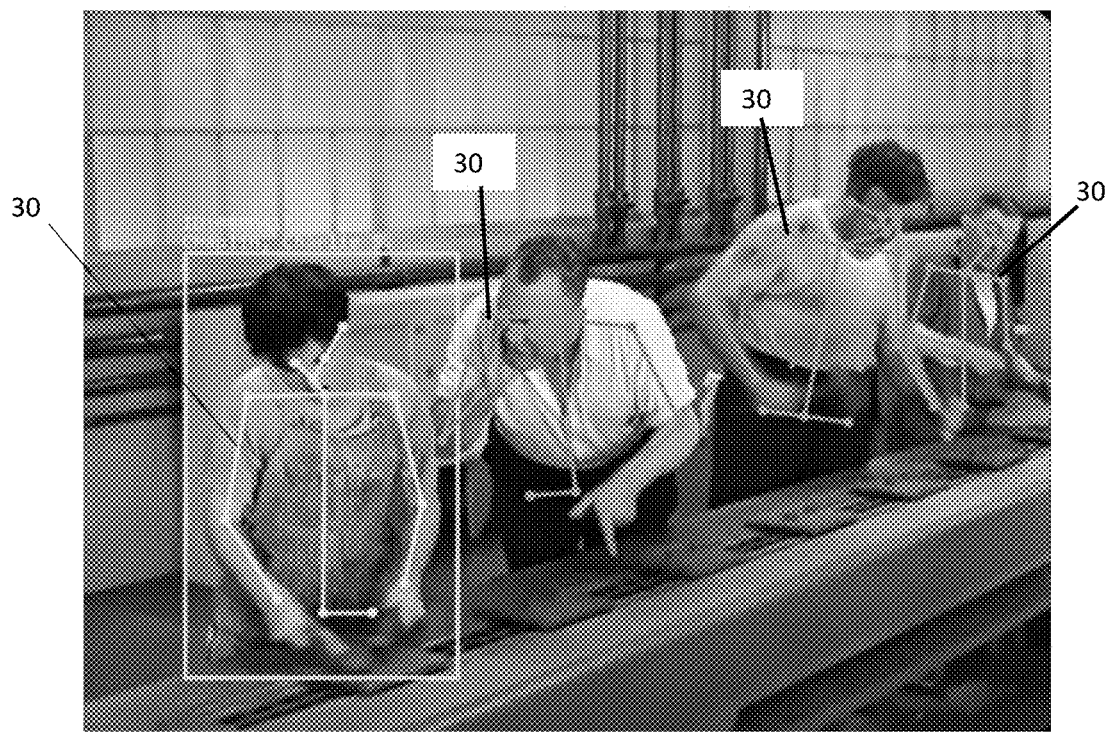
FIG. 7 illustrates feature maps generated on an image of a video feed of several workers that have been detected and tracked based on image data sent to the computing device.

FIG. 6 illustrates a feature map 30 for a single worker that has been detected and tracked based on image data sent to the computing device 16. FIG. 7 shows feature maps for several workers within a single image. The feature map preferably tracks several landmarks and joints (represented by dots in FIGS. 6 and 7) on each worker to aid in ergonomic analyses. In a preferred embodiment the following joints and landmarks may be tracked: left hip; right hip; chest; neck; left shoulder; right shoulder; left elbow; right elbow; left wrist; right wrist; left knee; right knee; left ankle; right ankle; nose; left ear; right ear; left eye; and right eye. Additionally, other joints and landmarks may be tracked, such as individual fingers and feet. Each of the landmarks and joints are tracked and compared for each frame to generate a kinematic configuration of each person. Examples of maps of the kinematic configuration of workers can be seen in FIGS. 6 and 7.

The algorithm first generates person detection bounding boxes. The objective here is to find pixels that correspond to a person and set a tight encompassing box around those pixels. When there are multiple instances of person detection, a bounding box should be created for each of those instances. A bounding box is represented as an ordered 4-tuple b=(x, y, w, h), where x, y are the coordinates of the center of the bounding box and w, h denote the width and the height dimensions. The problem of detecting person bounding boxes can be boil down to a problem of estimating an ordered tuple b for each person in the video frame.

With the success of CNNs, there has been a noticeable progress in computer vision research regarding fast and accurate detection of bounding boxes. For a given H×W image X, a CNN backbone produces a multi-channel activation map $F_i$ of the size $H_i \times W_i \times C_i$ at each layer, where $H_i < H$ and $W_i < W$ are the height and width of the activation maps and $C_i$ is the number of channels corresponding to different convolution filters (features). The activation map $F_i$ is a high-level, localized visual summary of the input image X around each grid points of the $H_i \times W_i$, represented by a $C_i$-dimensional vector at each location. Therefore, depending on the type of objects and their locations in the image, the activation map $F_i$ will have different $C_i$-dimensional vector at each of the $H_i \times W_i$ grid locations.

In fact, many state-of-the-art object detection algorithms use this intuition for bounding box detection. Here, a typically made assumption is that there can only be one (or a fixed number of) object per each of the $H_i \times W_i$ grid locations at each layer, given that the grid cells are small enough to resolve different objects of interest. Further, the idea of anchor boxes is commonly used in relevant literature [ref], which assumes a fixed number of different bounding boxes with predefined aspect ratios and scales, in order to avoid searching for infinitely many combinations of bounding box dimensions. In this work, we use k=5 different aspect ratios:

$$1 \times 1, 1 \times \frac{2}{3}, 1 \times \frac{1}{2}, 1 \times \frac{2}{5}, \text{ and } 1 \times \frac{1}{3} (\text{Height} \times \text{Width}).$$

A preferred embodiment uses vertical bounding boxes, as opposed to the other generic computer vision object detection algorithms. This is especially well suited to detecting people in manufacturing plants, who primarily are standing or sitting on a stool, etc. A multi-scale bounding box detection scheme, where each of the layers makes bounding box predictions at $H_i \times W_i$ grid locations may be used. The scale of the bounding box at each layer is determined such that the layers at different resolution can span varying sized objects from small to large:

$$S_i = s_{min} + \frac{s_{max} - s_{min}}{m - 1}(i - 1)$$

where i=1, ..., m are the index of layers that contributes to the bounding box prediction ordered from shallow (high-resolution) to deep (low-resolution) and $s_{min}$ and $s_{max}$ are the lowest and the highest scale of the bounding box with respect to the image size, respectively. In this work, we set $s_{min}=0.4$ and $s_{max}=0.9$ with respect to the height of the video.

For the prediction, each location in the $H_i \times W_i$ grid produces k=5 bounding box predictions. For each of the k bounding box predictions, the bounding box offsets $\Delta b=(\Delta x, \Delta y, \Delta w, \Delta h)$ and a binary class score c (1: person, 0: negative) are predicted. This yields k(4+1)=25 bounding box predictions at each grid location. For a DenseNet-121 backbone, the predictions are made before each of the transition blocks, producing $$\frac{H}{4} \times \frac{W}{4} \times 256, \frac{H}{8} \times \frac{W}{8} \times 512, \frac{H}{16} \times \frac{W}{16} \times 1024, \text{ and}$$

$$\frac{H}{32} \times \frac{W}{32} \times 1024$$

activation maps. For an input video size of 224×224, this is equivalent to 4,165 grid points, generating a rich set of candidate bounding boxes for the detection problem.

The training objective of the person detection network is defined by two loss function terms $L_{person}$ and $L_{box}$ forming a multi-task loss function $L = \alpha L_{person} + L_{box}$. The first term $L_{person}$ is the binary cross-entropy loss (log loss) for the person detection incidents, penalizing misclassification of person/non-person:

$$L_{person} = -\frac{1}{N}\left[\sum_{j \in person} \log(c_j) + \sum_{j \in neg.} \log(c_j)\right]$$

where N is the number of detected bounding boxes indexed by j and $c_j \in [0,1]$ is a predicted class score (1: person, 0: negative). When there is no detection (N=0) in the training image, $L_{person}$ is set to zero. The second term $L_{box}$ is the smooth L1 loss [ref] between the predicted bounding box and the ground truth bounding box as they are less sensitive to outliers. Given a predicted anchor box's coordinates ($p_x$, $p_y$, $p_w$, $p_h$) and its corresponding ground truth bounding box coordinates ($g_x$, $g_y$, $g_w$, $g_h$), we learn scale-invariant transformation $\Delta x$ and $\Delta y$ between the centers:

$$p'_x = p_x + p_w \Delta x, \; p'_y = p_y + p_h \Delta y$$

and the log-scale stretching $\Delta w$ and $\Delta h$ in width and heights, respectively:

$$p'_w = p_w \exp(\Delta w), \; p'_h = p_h \exp(\Delta h)$$

With this setup, the targeted values ($t_x$, $t_y$, $t_w$, $t_h$) for the prediction ($\Delta x$, $\Delta y$, $\Delta w$, $\Delta h$) are represented as:

$$t_x = \frac{g_x - p_x}{p_w}, \; t_y = \frac{g_y - p_y}{p_h}$$

-continued $$t_w = \log\left(\frac{g_w}{p_w}\right), t_h = \log\left(\frac{g_h}{p_h}\right)$$

Finally, the bounding box loss term $L_{box}$ is the smooth L1 loss between the target and the prediction:

$$L_{box} = \sum_{j \in person} \varphi(t_x - \Delta x) + \varphi(t_y - \Delta y) + \varphi(t_w - \Delta w) + \varphi(t_h - \Delta h)$$

where $\varphi$ is the smooth L1 loss function:

$$\varphi(x) = \begin{cases} 0.5x^2, & \text{if } |x| < 1 \\ |x| - 0.5, & \text{otherwise} \end{cases}$$

Bounding Box Tracking

The result of person detection is a set of discrete bounding boxes detected for each video frame, agnostic to the other adjacent video frames. Hence, the trajectories of the bounding boxes in the initial detection results are not smooth and the indices of the bounding boxes are inconsistent across video frames. Moreover, due to false negatives of the detection results, a person might be missing in some video frames. Similarly, due to false positives, "ghosts" might be detected, adding noise to the bounding box detection result. Furthermore, in some cases, a person of interest moves out of the camera angle but comes back after several video frames. To address all of these, a tracking algorithm for the detected bounding boxes is necessary.

A preferred tracking algorithm is a variant of Deep SORT algorithm described as follows. Similar to Deep SORT, our algorithm begins with some trackers initialized at the bounding boxes detected in the first frame of the video. We assume that we know a state-transition function that allows the prediction of next bounding box locations based on the previous trajectory. With a state-transition function, we predict the next location of the bounding boxes. For a given set of tracker-predicted person bounding boxes and the CNN-detected person bounding boxes, we solve an optimal assignment problem such that the tracker results are matched with the nearest bounding box detection results. If the matched bounding boxes are far apart from the prediction beyond a threshold, then we treat the prediction unassigned, which increase the internal counter in the tracker. If there is a bounding box that is not matched to a tracker, a new tracker is initialized at that location. We repeat this process across the entire video frames. When the tracker ages beyond a threshold, we consider we lost the objects and terminate the tracker.

Furthermore, we equip each of the trackers with an adaptive appearance model. The adaptive appearance model records the visual information within the bounding box and builds an adaptive statistical model to describe the appearance of the object detected by the bounding box. The adaptive appearance model is used to solve the assignment problem mentioned earlier, or to merge two different trackers for cases where the person of interest is lost due to false negatives or out-of-angle in the middle of the video.

Below are the detailed descriptions of each component:

Kalman Filter Trackers

A Kalman filter may be used as a tracking model since it provides an efficient yet reliable tracking performance. The Kalman filter is a recursive tracker that estimates the physical state of the object being tracked via repetition of the two distinct phases, namely, "prediction" and "update" phases. The basic idea of the Kalman filter in the context of bounding box tracking is as follows. First of all, the state of a bounding box is defined as $x=[b,\dot{b}]^T=[x, y, w, h, \dot{x}, \dot{y}, \dot{w}, \dot{h}]^T$, where the single dot accent indicates the first order derivative with respect to time, or the rate of change of the variable. Given such a definition of the state vector, the Kalman filter first estimates the current state, or a priori state, of the object based on the previous trajectory using some state transfer function. In this work, a Markov chain with the linear transfer function is assumed, or in other words:

$$x_{k|k-1} = F_k x_{k-1|k-1}$$

where $x_{k|k-1}$ is a priori state estimate derived from the previous state $x_{k-1|k-1}$, and $F_k$ is the state transfer function. The accuracy of estimation is approximated by another recursive relation $P_{k|k-1}=F_k P_{k-1|k-1} F_k^T Q_k$ where $P_{k|k-1}$ is the a priori covariance matrix estimating the accuracy of the state estimate and $Q_k$ is a covariance matrix determining the process noise $w_k \sim \mathcal{N}(0, Q_k)$. After the prediction is made, a priori state $x_{k|k-1}$ is combined with new measurements to produce updated, a posteriori state $x_{k|k}$ via the relationship $x_{k|k}=x_{k|k-1}+K_k y_k$, where $K_k$ is the Kalman gain and $y_k$ is the residual. Here the residual $y_k$ is computed based on the detected bounding box location $z_k$ assigned from the person detection algorithm so that $y_k=z_k-Hx_{k|k-1}$, where H is the measurement matrix defined as follows:

$$H = \begin{bmatrix} 1 & 0 & 0 & 0 & 0 & 0 & 0 & 0 \\ 0 & 1 & 0 & 0 & 0 & 0 & 0 & 0 \\ 0 & 0 & 1 & 0 & 0 & 0 & 0 & 0 \\ 0 & 0 & 0 & 1 & 0 & 0 & 0 & 0 \end{bmatrix}$$

In addition, we add internal counters to the Kalman filter trackers. The role of internal counters is to count how many consecutive frames that the tracker has been relying on its guess, without an assigned bounding box detection result. We set the age limit to the Kalman filter trackers so that trackers without assigned bounding boxes for more than a certain number of consecutive frames die out.

Furthermore, each of the Kalman filter trackers is associated with an adaptive appearance model. The adaptive appearance model records the history of visual appearances. The CNN-feature map at the tracked bounding box region is cropped for each frame and warped into a 32×32 map (i.e. ROI pooling). Here, to avoid storing 32×32 feature maps for a large number of video frames per tracker naively, we use the adaptive principal component analysis (PCA) model. The adaptive PCA model compresses a large set of feature maps by using the mean image and principal components. Instead of finding principal components each time a new cropped image is added, which involves the computationally-heavy eigendecomposition calculation repeatedly, adaptive PCA allows updating the mean and the principal components using an update formula. The adaptive appearance model tracked in this manner is used to merge two Kalman filter trackers and to solve the assignment problem.

After processing the entire video frames with the Kalman filter trackers, we compare the similarity among trackers using the appearance model. The dissimilarity between the trackers is defined as the weighted sum of the Euclidean distance between PCA means and the cosine distance between the principal components.

One of the key variables in the Kalman filter equations is the residual $y_k$ evaluated from a priori state $x_{k|k-1}$ and the detected bounding box location $z_k$ by the person detection algorithm. In our formulation, there are multiple Kalman filter trackers produce a priori states $x_{k|k-1}^{(i)}$, which need to be matched with multiple bounding box detection results $z_k^{(j)}$. Therefore, for each time step of the Kalman filter algorithm, an assignment problem needs to be solved between trackers indexed by i and detection results indexed by j. Here, similar to the original Deep SORT algorithm, we use the Hungarian algorithm to solve the optimal assignment problem between trackers and person detection results. For this, we define three metrics, namely the dimension similarity, feature similarity, and the adaptive appearance similarity. The dimension similarity promotes the Hungarian algorithm to assign bounding boxes at the similar position and size to the previous frame and is defined as:

$$d_{dimension}(i,j) = (b^{(i)} - z^{(j)})^2$$

where $b^{(i)}$ is the bounding box coordinates of the i-th Kalman filter tracker and $z^{(j)}$ is the CNN-detected bounding box coordinates.

In addition, the feature similarity measure compares the CNN-produced feature maps so that the bounding boxes are assigned to visually similar tracker locations. For this, we compare the cosine similarities between the Kalman filter tracked bounding boxes and the CNN-produced bounding boxes in the CNN-feature space. To achieve this, we crop the CNN-feature maps around the Kalman filter tracked bounding boxes and CNN-produced bounding boxes and represent them as descriptors $r^{(i)}$ and $r^{(j)}$, whose magnitudes are normalized to $\|r^{(i)}\| = \|r^{(j)}\| = 1$. The feature distance between the i-th Kalman filter tracked bounding box and the j-th CNN-produced bounding box is then defined as:

$$d_{feature}(i,j) = 1 - \langle r^{(i)}, r^{(j)} \rangle$$

where $\langle \cdot, \cdot \rangle$ denotes the dot product.

Finally, the adaptive appearance similarity computes the Mahalanobis distance between the feature map of a CNN-detected bounding box and the adaptive appearance model of a Kalman filter tracked bounding box and is defined as:

$$d_{appearance}(i,j) = (a^{(i)} - r^{(j)})^T \wedge^{-1} (a^{(i)} - r^{(j)})$$

where $\wedge^{-1}$ is the PCA covariance matrix.

We combine these three matrices using a weighted sum $$d(i,j) = \alpha d_{dimension}(i,j) + \beta d_{feature}(i,j) + \gamma d_{appearance}(i,j)$$

The Hungarian algorithm uses the weighted sum to determine the assignment between Kalman filter tracker bounding boxes and CNN-detected bounding boxes. After the assignment is completed, we select only admissible assignments, by thresholding each of the similarity measures. That is, if the bounding box positions and sizes are too distinct or the appearances are too different, we call it inadmissible assignment and discard the result. On unassigned CNN bounding boxes, new trackers are spawned, while for unassigned Kalman filter trackers, the internal counter increases.

Skeleton Detection

For each of the tracked bounding boxes, we detect 2D kinematic configuration of the person in the bounding box. Here, the input to the algorithm is a bounding box cropped video frame of an individual and the output is a 2D skeleton representing the kinematic configuration of body parts. The same DenseNet-121 backbone is re-used to reduce the computational overhead and to generate a multi-scale feature map F. The map F is then fed into the part affinity field (PAF) detection network first, to obtain the PAF map P. The PAF map P is then concatenated with F to augment the feature map, which then feeds the key point detection network. The final output of the key point network M alongside the PAF map P is used for skeleton parsing.

Key Point Detection

According to one embodiment, key landmark locations on the human body are detected. For the key point detection, we use a fully-convolutional neural network, which produces a heat map showing the likelihood of body joints across different pixel locations. For the training images, the ground truth heat maps are generated by putting the Gaussian peaks at the ground truth key point locations.

$$M_i(p) = \exp\left(-\frac{\|p - k_i\|}{\sigma^2}\right)$$

where $M_i$ is the ground truth heat map for the key point i, p is a pixel location in $M_i$, and $k_i$ is the ground truth location of the key point i.

Therefore, the role of the key point detection network is to produce heat maps that are as close as possible to the ground truth heat maps. If the key point detection network is represented as a function $f_{key}$, then the objective of training the key point detection network is $$L_{key} = \sum_i \left\| f_{key}^{(i)}(F) - M_i \right\|_F^2$$

The architecture of the key point detection network is comprised of a stack of 3×3 convolution layers, each followed by the rectified linear unit (ReLU) activation. To mitigate the vanishing gradient problem, there are skip connections every other layers of 3×3 convolutions, similar to the residual blocks in the ResNet architecture [ref]. At the end of the key point detection network, we set two layers of 1×1 convolution with ReLU activation.

Part Affinity Fields

Part affinity fields (PAF) are used to facilitate the skeleton parsing and to improve the confidence of key point detection. A PAF is a 2D vector field representing the association between body key points. If pixel locations p and q are body key points that are directly associated (e.g., elbow and wrist, hip and knee) and x is some point in-between p and q, the PAF between p and q at x is defined as a vector field:

$$PAF(x) = f(x) = \begin{cases} \dfrac{q-p}{\|q-p\|}, & \text{if } x \text{ is on body and between } p \text{ and } q \\ 0, & \text{otherwise} \end{cases}$$

Whether a point is on the body or not is determined by using the person segmentation mask provided in the ground truth data. Whether an on-body point is in-between key points p and q or not is determined simply by the dot product between the vectors p-q and x-q and the dot product between the vectors q-p and x-p: if any the angles determined by the dot products are over 90 degrees, x is not in-between the key points. These conditions, however, are insufficient in cases when there is a self-occlusion between body parts. To this, we set a thickness threshold, limiting the width of the limbs to a certain range.

The accuracy of PAF detection is determined based on the following loss function:

$$L_{PAF} = \sum_i \left\| f_{PAF}^{(i)}(F) - P_i \right\|_F^2$$

where $f_{PAF}$ is a PAF detection network that has the same architecture as the key point detection network and $P_i$ is the ground truth PAF for the i-th association between key points.

Skeleton Tracking

Skeleton tracking step is similar to the bounding box tracking step. The state space of the skeletons is defined a particle filter approach is used to track the skeleton. For the tracking of the detected skeletons, we define the following state space representation. First, consider a graph $\mathcal{G} = \{\mathcal{N}, \mathcal{E}\}$ representing a skeleton, where $\mathcal{N}$ is the graph nodes corresponding to the set of body key points and $\mathcal{E}$ is the graph edges connecting the body key points (i.e. bones). We set the head as the root node for the advantage of tracking, as the head region tends to provide stronger and richer visual cues and features effective for detection and tracking. Furthermore, the head and face regions are perceptually more important in human cognition that people recording the video tend to put efforts to keep the head area within the camera angle, while other body parts are easily clipped off. Therefore, although many representations of human kinematics in computer graphics, vision, robotics, and biomechanics tend to assume pelvis as the root node, a preferred mechanism is to use the head as the root for the task of visual human tracking.

Given the definition of skeleton topology, one way to define the kinematic configuration of the skeleton $\mathcal{G}$ is by defining the orientations $\phi_e$ and lengths $l_e$ of the bones $e \in \mathcal{E}$, alongside the global position t and orientation $\psi$ of the root node. For instance, for a bone e, if we use p to denote its parent, the position $t_e$ of the proximal joint of e (i.e. the point at which e joins with p) is determined from the configuration of the parent p. When the proximal joint of e is the root joint, then the proximal joint position $t_e$ is the same as the global position t. Similarly, the bone e inherits the orientation of the parent p and for the bone whose proximal joint is the root inherits the global orientation $\psi$.

Based on such kinematic representation, we define the state space representation of a skeleton as a vector $x = [t, \dot{t}, \psi, \dot{\psi}, \phi, \dot{\phi}, l, \dot{l}]^T$, where $\phi = [\phi_e]$ is a vector containing all the bone orientations, $l = [l_e]$ is a vector listing bone lengths, and the accent $\dot{x}$ represents the first-order derivative with respect to the time variable $$\left(\frac{\partial x}{\partial t}\right).$$

This is going to be the base representation for the tracking algorithm discussed here.

For the tracking of skeletons, particle filter trackers are used. Particle filter trackers have been widely used in the computer vision literature and applications, including model-based human pose tracking. A particle filter can be intuitively understood as a non-linear, non-Gaussian generalization of Kalman filter using the Monte Carlo method. At the highest level, a particle filter begins with a number of state estimation samples (particles) $x^{n=1, \cdots, N}$. The importance weight $p(x_{t-1}|z_{1:t-1})$ for each of the particles is computed. The particles are then re sampled according to the importance weights. A state transfer function (the motion model) is then applied to the resampled particles, to give rise to the new states $x_t$. Random noises are applied during this step, to "diffuse" the particles to model the uncertainty of the state transfer function. A particle filter repeats such a process of importance-weighted sampling and prediction to track the dynamics of the target object.

From the skeleton tracking standpoint, N random skeletons are drawn around the person of interest in the first frame, according to the Gaussian distribution whose mean is the CNN detected skeleton state of the person. Then in the next frame, the importance weights for the skeleton samples are computed based on the CNN detected skeleton. When multiple skeleton detections exist, the bounding box tracking result (Section 4) is used to solve the assignment problem. Here the measurement z is the CNN-generated key point heat map and PAF and the particle weights are computed based on how well the skeleton is aligned with the heat map and the PAF. The alignment with the heat map can be straightforwardly measured simply by sampling the heat map values from the skeleton joints. The alignment with the PAF is measured by computing the integral of dot product between the bone vector (a vector connecting the joints) and the PAF field. Particle skeletons weighted as such are then resampled accordingly, and the configuration of the particles are predicted based on the linear movement model. This process is repeated for all video frames and for all persons of interest.

3D Reconstruction

A 3D pose estimation is formulated as a regression problem in which the independent variables include adjacent video frames at times $[t-\Delta t, t+\Delta t]$ and their 2D pose estimation results and the dependent variable is a 3D posture at time t. Here, a naïve representation of the dependent variable (i.e., 3D posture) using joint angles or positions may lead to many implausible configurations, beyond physical limits of human body movement. To this end, the 3D body configuration is represented strictly on the motion manifold.

The motion manifold is a high-dimensional surface embedded in the joint configuration space where the 3D body configuration and the kinematics is physically plausible. If the joint configuration space is a space of all numerically possible 3D body kinematics without regarding the physical joint and movement limits of actual human, the motion manifold is a thin subset of the joint configuration space where the motions and configurations are physically likely for actual humans.

The motion manifold is estimated from data sets where 3D motion measurements of people are available. The Carnegie Mellon University Motion Capture (CMU MoCap) data set is preferred, but other relevant data sets can also be used, as long as the data set contains the 3D kinematics measurement and their corresponding (time-synced) video recording data. Without the loss of generality, a 3D motion data can be represented as a sequence of state vectors $x_t$ representing the kinematic state of the human body. The state vector $x_t$ consists of the joint rotations $\phi_j$ and limb lengths $l_{ij}$ at time t. The joint rotations $\phi_j$ are the elements of the special orthogonal group, SO(3), and are represented by 3×3 rotation matrices $R_j$, satisfying the relation $R_j^T R_j = R_j R_j^T = I$ and $\det(R_j) = 1$.

The goal is to find a parametric representation $f$ of the motion manifold and its inverse. Specifically, the intent is to the mapping $f$ that maps a motion state $x_i$ in the state space to a parameter $z_i$ in the vector space. The encoder-decoder neural networks model function $f$ and its inverse. A constraint to this formalization is that some elements of the motion state vector are in the space of SO(3) and are not closed to the addition or the scalar multiplication. Hence, a direct application of an encoder-decoder network does not guarantee the output to valid in the state space. To address this issue, we project the elements of SO(3) to its Lie algebra $\mathfrak{so}(3)$ via a logarithmic map. The elements of $\mathfrak{so}(3)$ are 3×3 skew-symmetric matrices which are closed to the vector space operations (the addition and the scalar multiplication). This means that the elements of $\mathfrak{so}(3)$ can be freely multiplied by a scalar and added to another element of $\mathfrak{so}(3)$ within the neural networks. The final output of the neural network, which is yet again in $\mathfrak{so}(3)$, can be projected back to SO(3) via the exponential map [ref].

The result of training such a SO(3) valued encoder-decoder network is a facility to parametrically represent an arbitrary human body posture with much fewer degrees of freedom than the original state space representation.

3D Pose Estimation

Using the parametric representation of the body configuration, a 3D pose estimation algorithm can be determined as follows. The inputs to the 3D pose estimation algorithm are a sequence of video frames at times $[t-\Delta t, t+\Delta t]$ and their 2D pose estimation results at each time t. From such inputs, we aim to predict a parameterized representation $z_t$ of the body posture on the motion manifold. This is a simple regression problem, where the goal is to regress some time series variables to $z_t$. To this, we use the temporal convolution idea as proposed in Pavllo et al. [ref:facebook_videopose3d]. The video frames are first convolved by reusing the same DenseNet-121 backbone. The feature map produced by the backbone is then flattened and concatenated by the state vector to form an input vector to the temporal convolutional network. The first layer of the temporal convolution takes immediate adjacent frames and produces hidden layer outputs. The second layer of temporal convolution takes hidden layer outputs from the frames further apart. Finally, the output of the second layer is then entered as an input to the motion manifold network which then constructs the 3D joint configuration.

For the training of such network, an online motion capture data base, such as the CMU MoCap data set is used, which provides 3D motion capture data of people in various different motions as well as their corresponding video images. The error of 3D estimation is quantified in terms of the mean squared error between the ground truth joint locations and the predicted joint locations and is minimized during the training of the 3D pose estimation network.

Joint Angles and Ergonomic Assessments

The time series of joint posture information is denoted $\theta_i(t)$, or the joint angle $\theta$ of movement i as function of time t. Numerical differentiation is used to generate a time series of joint movement velocity information from the time series of joint posture information, as follows:

$$v_i(t) = (\theta_i(t-1) - \theta_i(t+1))/(2 \times \Delta t)$$

wherein $\Delta t$ is the inverse of the video recording frame rate. In some cases, absolute value of $v_i(t)$ is taken to generate a time series of joint movement speed information, i.e.,:

$$sp_i(t) = |v_i(t)|$$

From $\theta_i(t)$, the following metrics of exposure are generated: the mean joint posture; the $5^{th}$, $10^{th}$, $50^{th}$, $90^{th}$, and $95^{th}$ and other selected percentiles of the cumulative joint posture distribution; the joint posture range, as the difference between the $95^{th}$ and $5^{th}$ percentiles or between the $90^{th}$ and $10^{th}$ percentiles; the proportion of recorded video in different categories of joint posture, the proportion of recorded video with neutral joint posture; the proportion of recorded video with extreme joint posture; the proportion of recorded video with neutral joint posture for at least three continuous seconds; and the number per minute of periods with neutral posture for at least three continuous seconds.

Joint posture categories may be defined as recommended by NIOSH. In some cases, the user can enter joint posture categorization schemes customized to their needs. Alternatively, thresholds for 'neutral' and 'extreme' postures can be derived from published literature known to those of ordinary skill in the art.

From $sp_i(t)$, the following metrics of exposure are generated: the mean joint movement speed, the $5^{th}$, $10^{th}$, $50^{th}$, $90^{th}$, and $95^{th}$ and other selected percentiles of the cumulative joint movement speed distribution; the joint movement speed range, as the difference between the $95^{th}$ and $5^{th}$ percentiles or between the $90^{th}$ and $10^{th}$ percentiles; the proportion of recorded video with low joint movement speed; the proportion of recorded video with high joint movement speed; the proportion of recorded video with low movement speed for at least three continuous seconds; and the number per minute of periods with low movement speed for at least three continuous seconds.

Using a combination of $\theta_i(t)$ and $sp_i(t)$, the following metrics of exposure are generated: the proportion of recorded video with both neutral posture and low velocity, the proportion of recorded video with both neutral posture and low velocity for at least three continuous seconds, and the number per minute of periods with both neutral posture and low velocity for at least three continuous seconds.

Identification and Reidentification

Each new worker identified in the video stream is compared to the feature map database to determine whether that person has an existing employee profile. If the employee is already in the database, the tracking information is added to that employee's profile. If the feature map of a new bounding box does not match an existing employee profile, a new profile is created. The database grows and continues to improve as it receives additional data. Accordingly, if a worker leaves the video frame and reenters later, say because the worker took a break, or needed to move to another area for a period, the worker will automatically be reidentified, without the need for additional external input such as signing in and out of a work area. According to one feature a display screen may permit a user to select an individual worker among several workers for analysis as illustrated in FIG. 7. A box or other marking may appear around the worker. The box may correspond to the coordinates of the bounding box for that worker. The name or other identification of the worker may appear in text form on the display screen. Line segments may be shown connecting the various landmarks and joints to illustrate the angles and positions being measured and recorded. The visual representation of the landmarks and joints using dots and line segments can be useful in verifying that the system is accurately mapping the correct features.

Ergonomic Analyses

Figure 8:
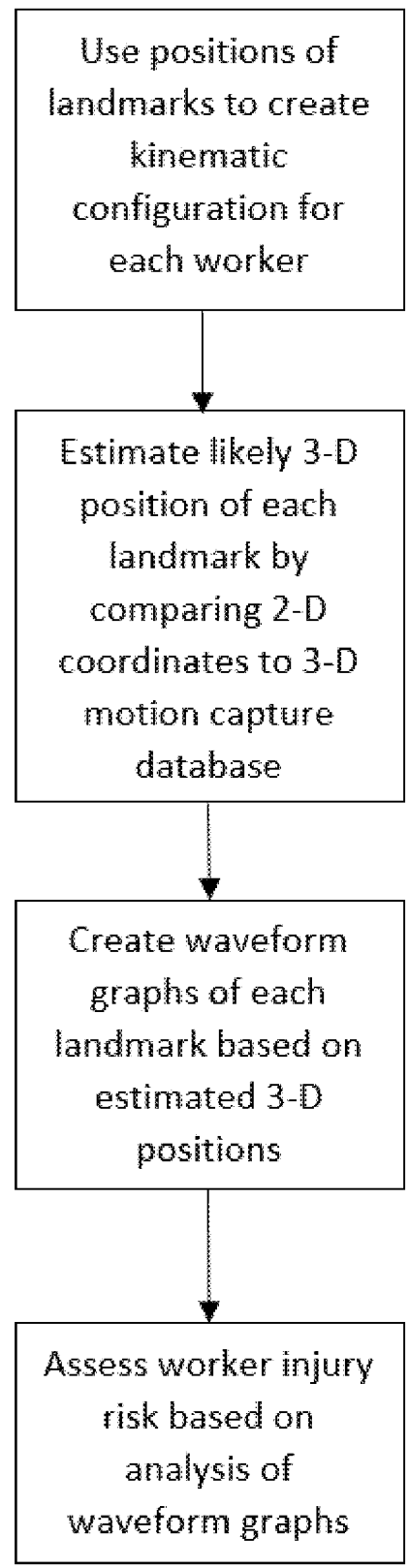
FIG. 8 is a flow chart showing an algorithm performed on a computing device to perform an ergonomic analysis of worker injury risks using waveform graphs information related to a worker's joints or other landmarks.

FIG. 8 shows an algorithm that can be used to perform an ergonomic assessment of worker risk based on the positions, angles, and velocities of the various joints and landmarks of tracked workers. The positions of the landmarks and joints are used to create the kinematic configuration for each worker, as shown in FIGS. 6 and 7. In essence, the 2-D coordinates of the landmarks and joints can be used to detect a 2-D posture for each person in each frame. The 2-D posture coordinates are compared to a 3-D motion capture database to estimate the likely 3-D posture of each worker in each frame, based on the 2-D coordinates of the landmarks and joints. Based on the likely 3-D postures of each worker in each frame, the joint angles and changes in joint angles over time can be calculated and recorded in that worker's database record. The system generates time-series continuous data that enables analysis of risk data. A worker within a video feed may be selected. His or her identifier, such as a name or number, may be displayed to confirm to which file in the database the information is being saved.

Figure 9:
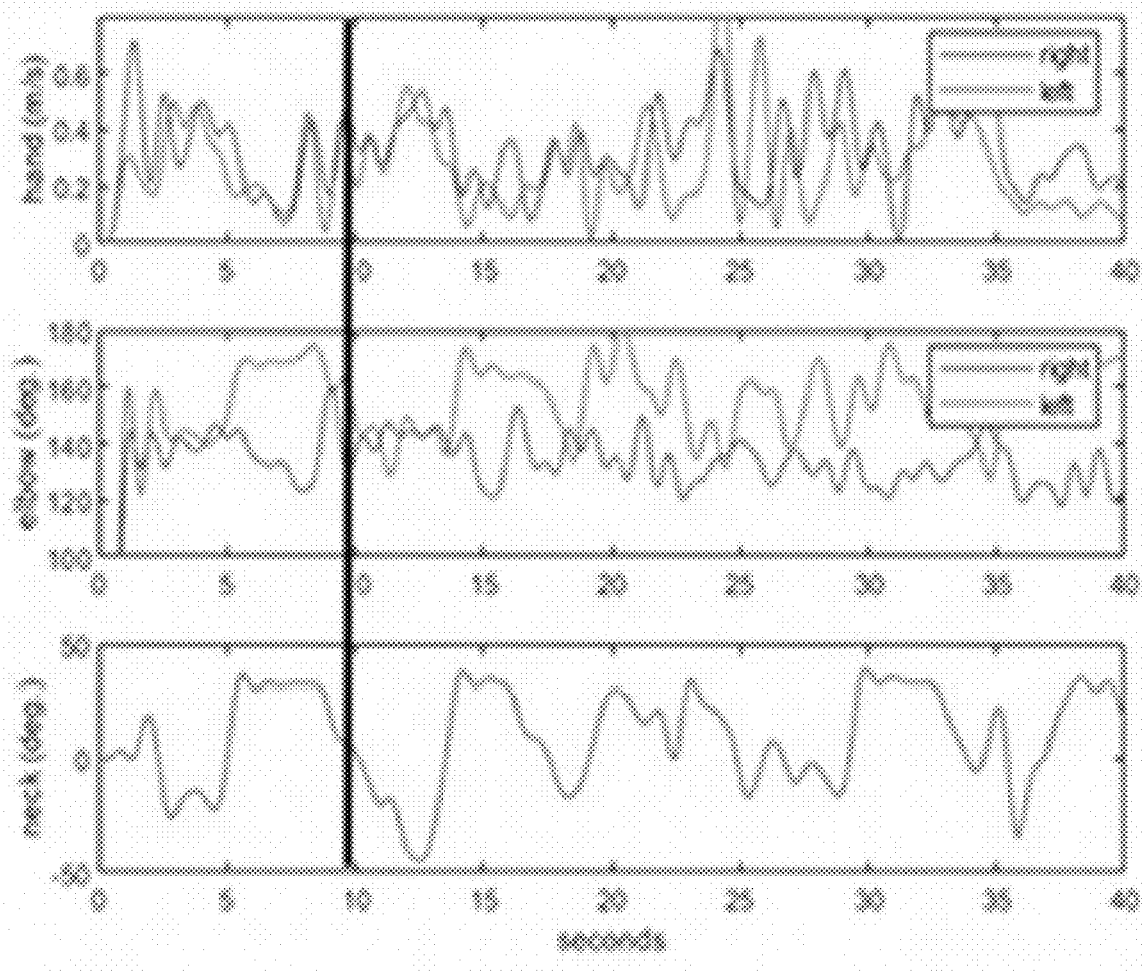
FIG. 9 is three waveform graphs of the hand movement, left and right elbow angular flexion, and neck angular flexion of the worker shown in FIG. 6.
Figure 10:
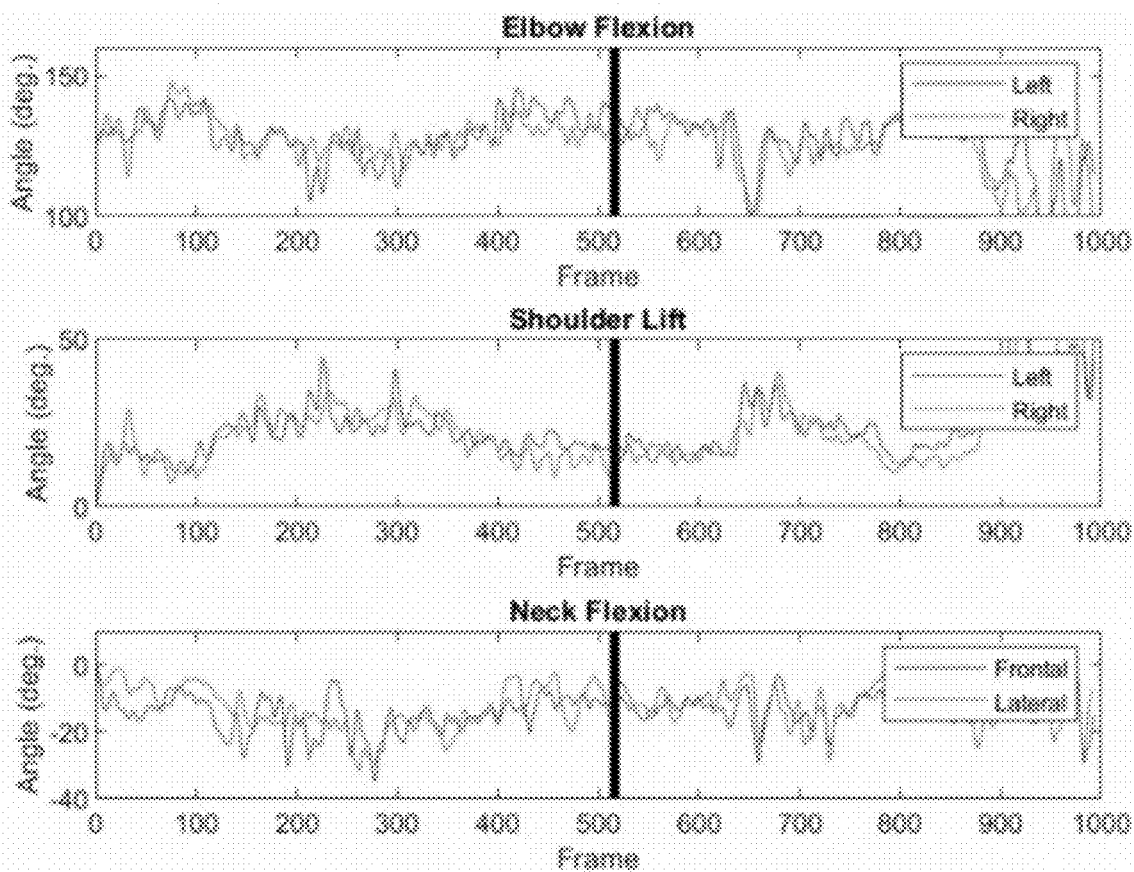
FIG. 10 is three waveform graphs of the elbow flexion, shoulder lift, and neck flexion of the selected worker of FIG. 7.
Figure 11:
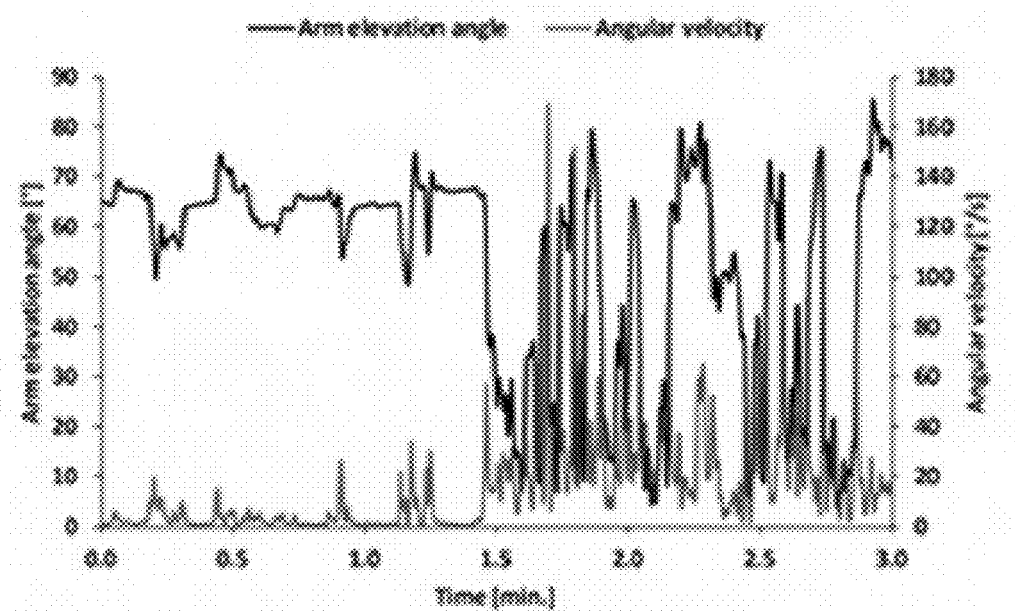
FIG. 11 is a waveform graph of the arm elevation angle and angular velocity of the arm of a worker.

Waveform graphs, as shown in FIGS. 9, 10, and 11 may be created and visually displayed for selected joints or markers. These waveform graphs can be compared with existing known waveform parameters to determine when workers are being exposed to higher risks.

This data is also useful for creating epidemiological data that can be used to study and measure the risks of various activities for the population of workers. This is especially useful for being data generated in the actual workplace rather than in an artificial laboratory setting.

The waveform data might also be useful for optimizing performance of workers. For examples the waveforms of high production or safer workers might be studied and used as examples for training new workers. Uses for the information gathered may include retraining workers and inboarding new employees. It can be used to interface with environmental and health data if desired. Integration with worker compensation financial data can occur. As well, there is the ability for workers to access their record and monitor their progress.

System for Collecting and Analyzing Data

Figure 12:
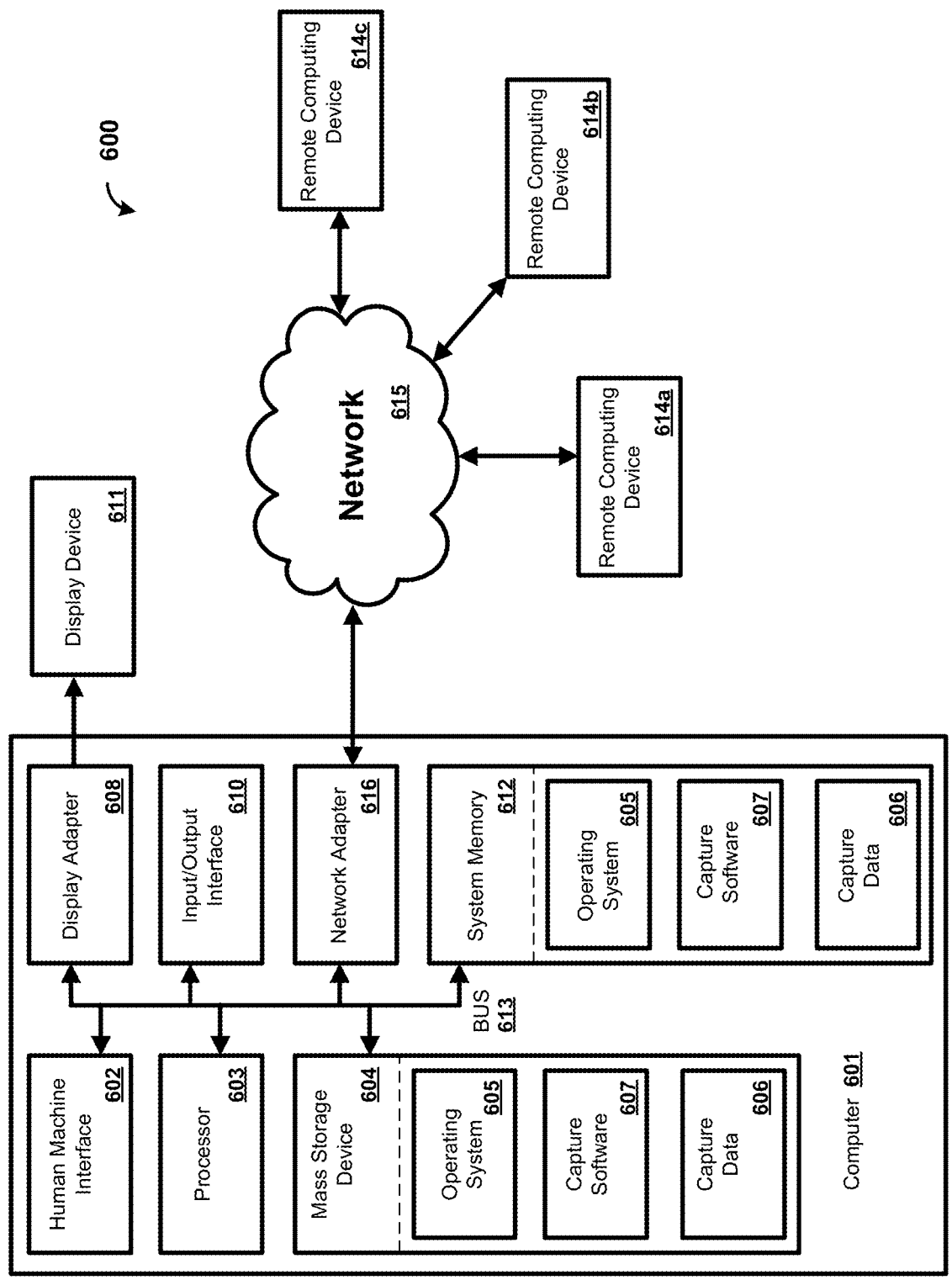
FIG. 12 shows a block diagram of an example computer.

FIG. 12 shows a system 600 for collecting data regarding kinematic movement and evaluating the same in accordance with the present description. The computer 601 may be used to gather and evaluate the data shown in FIGS. 9, 10, and 11. Each of the devices/entities shown in FIG. 1 may be a computer 601 as shown in FIG. 12. The computer 601 may comprise one or more processors 603, a system memory 612, and a bus 613 that couples various system components including the one or more processors 603 to the system memory 612. In the case of multiple processors 603, the computer 601 may utilize parallel computing. The bus 613 is one or more of several possible types of bus structures, including a memory bus or memory controller, a peripheral bus, an accelerated graphics port, or local bus using any of a variety of bus architectures.

The computer 601 may operate on and/or comprise a variety of computer readable media (e.g., non-transitory media). The readable media may be any available media that is accessible by the computer 601 and may include both volatile and non-volatile media, removable and non-removable media. The system memory 612 has computer readable media in the form of volatile memory, such as random access memory (RAM), and/or non-volatile memory, such as read only memory (ROM). The system memory 612 may store data such as the capture data 606 and/or program modules such as the operating system 605 and the capture software 607 that are accessible to and/or are operated on by the one or more processors 603.

The computer 601 may also have other removable/non-removable, volatile/non-volatile computer storage media. FIG. 12 shows the mass storage device 604 which may provide non-volatile storage of computer code, computer readable instructions, data structures, program modules, and other data for the computer 601. The mass storage device 604 may be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules may be stored on the mass storage device 604, such as the operating system 605 and the capture software 607. Each of the operating system 605 and the capture software 607 (e.g., or some combination thereof) may have elements of the program modules and the capture software 607. The capture data 606 may also be stored on the mass storage device 604. The capture data 606 may be stored in any of one or more databases known in the art. Such databases may be DB2®, Microsoft® Access, Microsoft® SQL Server, Oracle®, mySQL, PostgreSQL, and the like. The databases may be centralized or distributed across locations within the network 615.

A user may enter commands and information into the computer 601 via an input device (not shown). Examples of such input devices comprise, but are not limited to, a keyboard, pointing device (e.g., a computer mouse, remote control), a microphone, a joystick, a scanner, tactile input devices such as gloves, and other body coverings, motion sensor, and the like These and other input devices may be connected to the one or more processors 603 via a human machine interface 602 that is coupled to the bus 613, but may be connected by other interface and bus structures, such as a parallel port, game port, an IEEE 1394 Port (also known as a Firewire port), a serial port, network adapter 616, and/or a universal serial bus (USB).

The display device 611 may also be connected to the bus 613 via an interface, such as the display adapter 608. It is contemplated that the computer 601 may have more than one display adapter 608 and the computer 601 may have more than one display device 611. The display device 611 may be a monitor, an LCD (Liquid Crystal Display), light emitting diode (LED) display, television, smart lens, smart glass, and/or a projector. In addition to the display device 611, other output peripheral devices may be components such as speakers (not shown) and a printer (not shown) which may be connected to the computer 601 via the Input/Output Interface 610. Any step and/or result of the methods may be output (or caused to be output) in any form to an output device. Such output may be any form of visual representation, including, but not limited to, textual, graphical, animation, audio, tactile, and the like. The display device 611 and computer 601 may be part of one device, or separate devices.

The computer 601 may operate in a networked environment using logical connections to one or more remote computing devices 614*a,b,c*. A remote computing device may be a personal computer, computing station (e.g., workstation), portable computer (e.g., laptop, mobile phone, tablet device), smart device (e.g., smartphone, smart watch, activity tracker, smart apparel, smart accessory), security and/or monitoring device, a server, a router, a network computer, a peer device, edge device, and so on. Logical connections between the computer 601 and a remote computing device 614*a,b,c* may be made via a network 615, such as a local area network (LAN) and/or a general wide area network (WAN). Such network connections may be through the network adapter 616. The network adapter 616 may be implemented in both wired and wireless environments. Such networking environments are conventional and commonplace in dwellings, offices, enterprise-wide computer networks, intranets, and the Internet.

Application programs and other executable program components such as the operating system 605 are shown herein as discrete blocks, although it is recognized that such programs and components reside at various times in different storage components of the computing device 601, and are executed by the one or more processors 603 of the computer. An implementation of the capture software 607 may be stored on or sent across some form of computer readable media. Any of the described methods may be performed by processor-executable instructions embodied on computer readable media.

Summary

In summary the system and method are designed to obtain data associated with the repetitive work, the information comprising previous health and medical history of the workers, health-related habits of the workers, type and role of the workers at work, times of events of work-related musculoskeletal injuries, environmental conditions such as temperature of the workplace, motion capture of the workers at work. It generates a statistical model for the data associated with the repetitive work; evaluating individuals using quantitative scores; and reporting the injury risk scores to the employer.

Furthermore, the collection and analysis of a large volume of video data and over a prolonged period of time can, when paired with health outcome data collected at the worker level (e.g., work environment, demographics, symptom self-reports or clinical assessment) and/or at the organizational level (e.g., OSHA 300 or other records-based surveillance systems), lead to improved understanding of dose-response relationships necessary to optimize task and work design, decrease the number of injuries and decrease health care expenses for manufacturers.

This system, designed for automated analysis of ergonomics (body posture and positioning identification) for example for meat processing workers using the power of computer vision and deep machine learning, prevents and decreases drastically upper extremities musculoskeletal injuries associated with repetitive stress injuries and reduces the high costs associated with these injuries. In many ways this Prevention and Safety Management system (PSM) is a tremendous improvement, possibly even "an inflection point", in the way manufacturers presently monitor, prevent, and mitigate risks of work-related injuries.

This Prevention and Safety Management system improves upon available exposure assessment methods by:
(1) minimizing error in the estimation of working postures in comparison to commonly-used observation techniques,
(2) measuring, in addition to time spent in certain posture categories, additional kinematic variables that are important to musculoskeletal health (e.g., movement velocities, rest/recovery time, and variations in movement patterns, among others),
(3) substantially reducing the time needed for an analyst to complete existing assessment processes, and
(4) eliminating the need for equipping workers with wearable sensors.
(5) by pairing with health outcome data collected at the worker level (e.g., work environment, demographics, symptom self-reports or clinical assessment) and/or at the organizational level (e.g., OSHA 300 or other records-based surveillance systems), it leads to improved understanding of dose-response relationships necessary to optimize task and work design, decrease the number of injuries and decrease health care expenses for manufacturers.

Data input: Images collected from the video cameras (non-intrusive imaging sensors) are streamed to a server cloud to be analyzed.

Data analysis: Using the algorithm developed for this invention, specific workers and their type of activities are recognized, and images are analyzed continuously. Each body joint positions and angles are determined and measured (kinematic activities) and then parsed into metrics relevant to workplace ergonomics, such as number of repetitions, total distance travelled, range of motion, and the proportion of time in different posture categories.

Data output:
  i. Ergonomic specialists and safety engineers receive immediate information on each individual worker and on group of workers (see FIG. 4).
  ii. The information is segmented to give general information on walk/posture, and specific information on lift, push, pull, reach, force, repetition, duration . . . for each joint of interest.
  iii. The safety engineers can rapidly determine and grade the risk of injuries for each individual worker.
  iv. Based on the data analysis using deep machine learning algorithm, recommendations to prevent worker injuries are made available to the safety engineers.
  v. Feeding these data into an Ergonomic Assessment System, the system will automatically populate current exposure assessment tools that require estimation of working postures (see FIG. 4).

From the above description, many unique characteristics not presently available in the known art could be apparent from the system and method herein described. For example, it is configurable to meet any particular industrial jobs unique needs. It is easy and rapid to access. Provides quick suggestive or corrective actions which when needed are easy to follow-up and allows the ability to write notes to individual workers from the observed data. One can observe an individual worker throughout multiple areas in the same plant or in different plants by looking at different videos. The system allows the ability to compare worker population to regional or national worker populations using ergonomic metrics.

While specific configurations have been described, it is not intended that the scope be limited to the particular configurations set forth, as the configurations herein are intended in all respects to be possible configurations rather than restrictive. Unless otherwise expressly stated, it is in no way intended that any method set forth herein be construed as requiring that its steps be performed in a specific order.

Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of configurations described in the specification.

It will be apparent to those skilled in the art that various modifications and variations may be made without departing from the scope or spirit. Other configurations will be apparent to those skilled in the art from consideration of the specification and practice described herein. It is intended that the specification and described configurations be considered as exemplary only, with a true scope and spirit being indicated by the following claims.

What is claimed is:

1. A non-transitory, processor-readable medium comprising code that when executed cause a processor to:
   receive two dimensional (2D) image data from an image capturing device positioned to capture image data of one or more workers simultaneously performing at least one task, the one or more workers not wearing motion tracking equipment;
   execute a machine learning model that includes a neural network and that is applied to the 2D image data to generate, using a motion manifold and in a special orthogonal group format, a set of joint positions and body angles of each worker from the one or more workers;
   execute a Monte Carlo Kalman filter to track at least one individual worker from the one or more workers;
   generate a landmarks map of multiple joints of the at least one individual worker;
   record positions and angular relations of the joints in the landmarks map in each frame of the 2D image data;
   generate a waveform graph for the at least one individual worker based on the recorded positions and angular relations; and
   assess future risks for the at least one individual worker based on an analysis of the waveform graph, the waveform graph including an angular flexion of a joint on one axis, an angular velocity of the joint on one axis and moments of time on a second axis.

2. The processor-readable medium of claim 1, wherein:
   the recorded positions of the joints are in two dimensions within each frame of the 2D image data; and
   the two-dimensional positions are used to estimate three dimensional positions of the joints.

3. The processor-readable medium of claim 1, further comprising code that when executed cause the processor to:
   select at least one performance metric from a plurality of performance metrics, each performance metric from the plurality of performance metrics associated with an ergonomic movement of the at least one individual worker, and
   generate at least one performance metric weight associated with the at least one performance metric, the at least one performance metric weight indicating a relative importance of the at least one performance metric compared to the remaining performance metrics from the plurality of performance metrics.

4. The processor-readable medium of claim 3, wherein the plurality of performance metrics include posture categories.

5. The processor-readable medium of claim 4, wherein the plurality of performance metrics further include at least one of (1) movement velocities, (2) rest times, or (3) variations in movement patterns.

6. The processor-readable medium of claim 1, code that when executed cause the processor to:
   recommend a course of action to address the future risks assessed for the at least one individual worker.

7. The processor-readable medium of claim 1, wherein the code to execute the machine learning model includes code to execute the machine learning model, without using data from wearable sensors, to determine ergonomic data related to posture, lift, pull, reach, force, repetition, and duration.

8. A system, comprising:
   a camera configured to simultaneously capture two-dimensional (2D) image data of a first worker and a second worker; and
   a computing device configured to be in communication with the camera to receive the 2D image data from the camera, the computing device being adapted to:
   execute a machine learning model that includes a neural network and that is applied to the 2D image data to generate, using a motion manifold and in a special orthogonal group format, a first set of joint positions of the first worker, a first set of body angles of the first worker, a second set of joint positions of the second worker, and a second set of body angles of the second worker,
   parse the first set of joint positions, the first set of body angles, the second set of joint positions, and the second set of body angles into metrics relevant to workplace ergonomics, and
   populate a worker risk assessment tool with the metrics relevant to workplace ergonomics to generate waveform graphs of the first set of joint positions, the second set of joint positions, the first set of body angels and the second set of body angles to predict a first worker future risk assessment of the first worker and a second worker future risk assessment of the second worker, each waveform graph including an angular flexion of a joint on one axis, an angular velocity of the joint on one axis and moments of time on a second axis.

9. The system of claim 8, wherein the computing device is a computing cloud.

10. The system of claim 8, wherein the metrics relevant to workplace ergonomics include posture categories.

11. The system of claim 10, wherein the metrics relevant to workplace ergonomics further include at least one of (1) movement velocities, (2) rest times, or (3) variations in movement patterns.

12. The system of claim 8, wherein the computing device is further adapted to recommend a course of action to address risks identified in the first worker future risk assessment and the second worker future risk assessment.

13. The system of claim 8, wherein the computing device is further adapted to execute the machine learning model, without using data from wearable sensors, to determine ergonomic data related to posture, lift, pull, reach, force, repetition, and duration.

14. The system of claim 8, wherein:
   the first worker future risk assessment includes information about a grade and risk of future injuries to the first worker; and
   the second worker future risk assessment includes information about a grade and risk of future injuries to the second worker.

15. The system of claim 8, wherein the computing device is adapted to execute the Monte Carlo Kalman filter to track the first worker and the second worker in frame-to-frame of the 2D image data.

16. The system of claim 8, the computing device is further adapted to:
- select at least one performance metric from a plurality of performance metrics, each performance metric from the plurality of performance metrics associated with an ergonomic movement of at least one of the first worker or the second worker, and
- generate at least one performance metric weight associated to the at least one performance metric, the at least one performance metric weight indicating a relative importance of the at least one performance metric compared to the remaining performance metrics from the plurality of performance metrics.

17. The method of claim 8, wherein the neural network of the machine learning model is a region-based convolutional neural network (R-CNN).

18. A non-transitory, processor-readable medium comprising code that when executed cause a processor to:
- execute a machine learning model that includes a neural network and that is applied to two-dimensional (2D) image data of a first worker and a second worker, to generate a first set of joint positions of the first worker, a first set of body angles of the first worker, a second set of joint positions of the second worker, and a second set of body angles of the second worker;
- parse the first set of joint positions, the first set of body angles, the second set of joint positions, and the second set of body angles into metrics relevant to workplace ergonomics; and
- populate a worker risk assessment tool with the metrics relevant to workplace ergonomics to generate waveform graphs of the first set of joint positions, the second set of joint positions, the first set of body angels and the second set of body angles to predict a first worker future risk assessment of the first worker and a second worker future risk assessment of the second worker, each waveform graph including an angular flexion of a joint on one axis, an angular velocity of the joint on one axis and moments of time on a second axis.

19. The processor-readable medium of claim 18, wherein:
- the 2D image data of the first worker and the second worker includes 2D image data of the first worker and the second worker simultaneously performing at least one task,
- the code to execute the machine learning model includes code to execute the machine learning model without using data from wearable sensors.

20. The processor-readable medium of claim 18, wherein:
- the code to execute the machine learning model includes code to execute the machine learning model using a motion manifold and in a special orthogonal group format of the 2D image data.

* * * * *